(12) United States Patent
Sablong et al.

(10) Patent No.: US 9,683,099 B2
(45) Date of Patent: Jun. 20, 2017

(54) INTEGRATED CIRCUIT WITH CO$_2$ SENSOR, COMPOSITION AND MANUFACTURING METHOD OF SUCH AN IC

(71) Applicant: ams International AG, Rapperswil-Jona (CH)

(72) Inventors: Rafael Sablong, Eindhoven (NL); Aurelie Humbert, Brussels (BE); Bjorn Tuerlings, Goirle (NL); Cornelis Bastiaansen, Montfort (NL); Dirk Gravesteijn, Waalre (NL); Dimitri Soccol, Rotselaar (BE); Jan Kolijn, Eindhoven (NL)

(73) Assignee: AMS INTERNATIONAL AG, Rapperswil-Jona (CH)

( * ) Notice: Subject to any disclaimer, the term of this patent is extended or adjusted under 35 U.S.C. 154(b) by 86 days.

(21) Appl. No.: 14/477,453

(22) Filed: Sep. 4, 2014

(65) Prior Publication Data
US 2015/0084100 A1    Mar. 26, 2015

(30) Foreign Application Priority Data

Sep. 26, 2013    (EP) .................................... 13186140

(51) Int. Cl.
*G01N 27/403*    (2006.01)
*C08L 53/00*    (2006.01)
(Continued)

(52) U.S. Cl.
CPC ............ *C08L 53/00* (2013.01); *G01N 27/126* (2013.01); *G01N 27/221* (2013.01);
(Continued)

(58) Field of Classification Search
None
See application file for complete search history.

(56) References Cited

U.S. PATENT DOCUMENTS

| 4,429,343 A | 1/1984 | Freud |
| 5,018,380 A | 5/1991 | Zupancic et al. |

(Continued)

FOREIGN PATENT DOCUMENTS

| CA | 2 539 418 A1 | 9/2007 |
| EP | 2 343 541 A1 | 7/2011 |

(Continued)

OTHER PUBLICATIONS

Endres, Hanns-Erik, et al; "A Capacitive CO$_2$ Sensor System with Suppression of the Humidity Interference"; Sensors and Actuators B 57; Elsevier; pp. 83-87 (1999).

(Continued)

*Primary Examiner* — Robert Bachner
(74) *Attorney, Agent, or Firm* — McDermott Will & Emery LLP

(57) ABSTRACT

Disclosed is an integrated circuit (100) comprising a semiconductor substrate (110) carrying a plurality of circuit elements (111); and a carbon dioxide sensor (120) over said semiconductor substrate, said sensor comprising a pair of electrodes (122, 124) laterally separated from each other; and a carbon dioxide (CO$_2$) permeable polymer matrix (128) at least partially covering the pair of electrodes, said matrix encapsulating a liquid (126) comprising an organic alcohol and an organic amidine or guanidine base. A composition for forming such a CO$_2$ sensor on the IC and a method of manufacturing such an IC are also disclosed.

14 Claims, 11 Drawing Sheets

Figure 1:
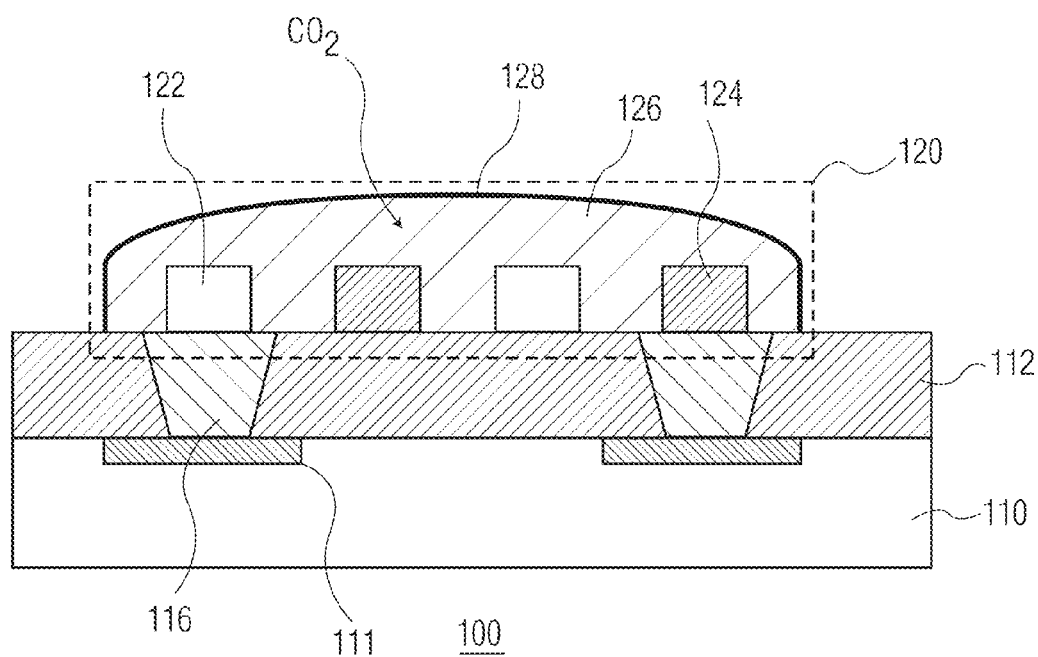

(51) Int. Cl.
*G01N 27/12* (2006.01)
*G01N 27/22* (2006.01)
*G01N 33/00* (2006.01)

(52) U.S. Cl.
CPC ......... *G01N 27/227* (2013.01); *G01N 33/004* (2013.01); *G01N 2027/222* (2013.01)

(56) References Cited

U.S. PATENT DOCUMENTS

| | | | |
|---|---|---|---|
| 6,222,376 B1 | 4/2001 | Tenney, III | |
| 6,690,569 B1 | 2/2004 | Mayer et al. | |
| 6,730,212 B1* | 5/2004 | Yamagishi | G01N 27/126 204/403.01 |
| 7,222,531 B2 | 5/2007 | Isogai et al. | |
| 7,982,069 B2 | 7/2011 | Jessop et al. | |
| 2011/0073164 A1* | 3/2011 | Solis | H01L 31/048 136/251 |
| 2011/0138878 A1 | 6/2011 | Serban et al. | |
| 2011/0146382 A1 | 6/2011 | Fleischer et al. | |
| 2011/0180884 A1* | 7/2011 | Lazarus | G01N 27/227 257/414 |
| 2014/0170762 A1* | 6/2014 | Soccol | G01N 33/004 436/133 |
| 2014/0191348 A1* | 7/2014 | Humbert | G01N 21/766 257/431 |
| 2015/0009503 A1* | 1/2015 | Shimoyama | G01N 21/553 356/445 |

FOREIGN PATENT DOCUMENTS

| | | | |
|---|---|---|---|
| JP | 2012-004964 | * | 1/2012 |
| WO | 2010/031047 A2 | | 3/2010 |
| WO | 2010/039479 A1 | | 4/2010 |

OTHER PUBLICATIONS

Guo, Zanru et al; "A novel smart polymer responsive to $CO_2$"; Chem. Commun., 47; pp. 9348-9350 (2011).

Heldebrandt, David J., et al; "$CO_2$-binding Organic Liquids ($CO_2$BOLs) for Post-Combustion $CO_2$ Capture"; Energy Procedia vol. 1, No. 1; Elsevier, NL; pp. 1187-1195 (Feb. 1, 2009).

Stegmaier, S. et al; "Sensing mechanism of room temperature $CO_2$ sensors based on primary amino groups"; Sensors and Actuators B: Chemical, 154(2), pp. 270-276 (2011).

Mazard, Cecile, et al: "Dynamic Mechanical Properties of Polystrene-based Block Copolymers Blended with poly (2,6-dimethyl-1, 4-phenylene oxide)";Polymer International, vol. 52, Issue 4; pp. 514-521 (Mar. 21, 2003).

Yu, Jian Ming et al; "Stereocomplexation of sPMMA-PBD-sPMMA triblock copolymers with isotactic PMMA: 1. Thermal and mechanical properties of sterocomplexes"; Polymer, vol. 38, No. 9; Elseiver Science Ltd, Great Britain; 13 pages (1997).

Extended European Search Report for application No. 13186140.3 (Feb. 28, 2014).

* cited by examiner

10 WT% DBU IN OLEYL ALCOHOL WITH DIFFERENT AMOUNTS OF KRATON G1652

AS APPLIED

30 WT% KRATON        50 WT% KRATON        70 WT% KRATON

AFTER EXPOSURE TO VIBRATION

EXAMPLE 1            EXAMPLE 2            EXAMPLE 3

INTEGRATED CIRCUIT WITH $CO_2$ SENSOR, COMPOSITION AND MANUFACTURING METHOD OF SUCH AN IC

CROSS-REFERENCE TO RELATED APPLICATIONS

This application claims the priority under 35 U.S.C. §119 of European patent application no. 13186140.3 filed on Sep. 26, 2013, the contents of which are incorporated by reference herein.

FIELD OF THE INVENTION

The present invention relates to an integrated circuit (IC) comprising a semiconductor substrate carrying a plurality of circuit elements; and a carbon dioxide sensor over said semiconductor substrate.

The present invention further relates to a composition for forming a carbon dioxide sensor over the substrate of such an IC.

The present invention yet further related to a method of manufacturing such an IC.

BACKGROUND OF THE INVENTION

Nowadays, integrated circuits (ICs) may comprise a plethora of sensors, such as gas sensors, relative humidity (RH) sensors, specific analyte detection sensors, and so on. Such sensors may be included in the IC design for a number of reasons.

For instance, a $CO_2$ sensor may be included in an IC to detect a change in the ambient conditions of a product tagged with the chip such that product quality control can be achieved by monitoring the sensor readings of the chip. This can for instance be used to accurately predict the remaining shelf life of the product, e.g. perishable food stuff, a pharmaceutical or biomedical product, or logistics-based applications. The sensor may for instance be adapted to determine changes in the $CO_2$ content of the ambient atmosphere. Alternatively, the sensor may be used to detect changes in the $CO_2$ composition of larger environments such as buildings, e.g. in heating ventilation and air conditioning (HVAC) applications, or may be used in medical application domains, e.g. in breathing apparatuses.

It is particularly relevant to mass market applications such as RF tags for product monitoring that the gas sensor functionality can be added to the IC with limited additional cost, as there is a large price pressure on such ICs; i.e. they have to be produced cheaply in order to be commercially attractive. This is not easily achieved, especially when there is a requirement for the sensor to have high, e.g. parts per million (ppm), $CO_2$ sensitivity, such as in HVAC applications where $CO_2$ levels may be below 1,000 ppm.

David J. Heldebrandt et al. in Energy Procedia 1 (2009), pages 1187-1195 disclose a new class of $CO_2$ absorbing materials, referred to as $CO_2$-binding organic liquids ($CO_2$-BOLs) that are neat (solvent-free) liquid mixtures of organic alcohols and organic amidine or guanidine bases, which undergo the following reversible reaction in the presence of $CO_2$:

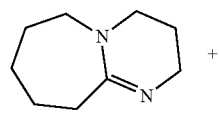

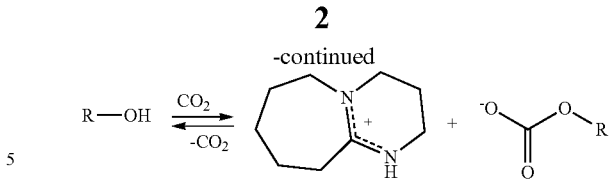

The $CO_2$ may be released by purging the $CO_2$-BOLS e.g. with $N_2$. In the above reaction scheme, DBU (diazabicyclo [5,4,0]undec-7-ene) is shown as the amidinium precursor, although Heldebrandt et al. disclose that a large variety of amidines and guanidines exhibit similar sensitivity to $CO_2$. Similarly, several alkyl alcohols, e.g. hexanol, may be used to form the alkylcarbonate anion. The $CO_2$ uptake was determined using conductivity measurements of the $CO_2$-BOL dissolved in acetonitrile, as the level of $CO_2$ uptake is (linearly) correlated to the conductivity of the solution. The authors recommend that the absorption capacity of a $CO_2$-BOLS can be increased by choosing a base and alcohol of low molecular weight, e.g. 1,1,3,3-tetramethylguanidine (TMG) and methanol. However, a challenge remains as to how to integrate a $CO_2$-BOL as a sensor material on an integrated circuit.

SUMMARY OF THE INVENTION

The present invention seeks to provide an integrated circuit comprising a $CO_2$ sensor that can be manufactured in a cost-effective manner whilst at the same time displaying ppm $CO_2$ sensitivity.

The present invention yet further seeks to provide a composition for forming such a $CO_2$ sensor on such an IC.

The present invention yet further seeks to provide a method of manufacturing such an IC.

In accordance with an aspect of the present invention, there is provided an integrated circuit comprising a semiconductor substrate carrying a plurality of circuit elements; and a carbon dioxide sensor over said semiconductor substrate, said sensor comprising a pair of electrodes laterally separated from each other; and a $CO_2$-permeable polymer matrix at least partially covering the pair of electrodes, said matrix encapsulating a solution comprising an organic alcohol; and an amidine or guanidine base, wherein the polymer matrix comprises a gel-forming block co-polymer.

The present invention is based on the provision of a manufacturing route in which a $CO_2$-BOL to be used as the $CO_2$ sensitive material in a $CO_2$ sensor on an IC can be immobilized or encapsulated in a $CO_2$-permeable polymer matrix predominantly formed of a gel-forming polymer.

In an embodiment, the gel forming polymer comprises a block co-polymer comprising at least one rigid block and at least one elastomeric block, also called a physical cross-linking polymer. In the context of the present invention, the term "physical cross-linking" refers to the intermolecular physical restraints that inhibit molecular mobility. For example, this is known from block copolymers, e.g. SBS (styrene-butadiene-styrene) block copolymers, comprising glassy or rigid ('hard') polystyrene domains encased in an elastomeric ('soft') polybutadiene matrix. The hard domains restrict the movement of the soft phase much as a chemical (e.g. covalent) crosslink behaves in crosslinked rubber, which has led to the definition of the term "physical cross-linking". In fact, to restrict movement of individual chains, forces between polymer chains based on hydrogen bonding, chain entanglements, ionic bonds in ionomers, and crystallites in a semicrystalline polymer all act in a similar manner. All of these forces can be used to form hard domains in a polymer matrix.

In the context of the present invention, the rigid block and the elastomeric block are defined by their respective glass transition temperatures $T_g$, where the rigid block has a higher $T_g$ compared to the elastomeric block. The rigid block has a $T_g$ preferably above the maximum temperature of the application temperature range, while the elastomeric preferably a $T_g$ below the minimum temperature of the application range.

In the context of the present invention, a block copolymer is a polymer comprising at least two different polymer blocks and is not intended to be limited to a copolymer containing exactly two different polymer blocks; instead, this term is also intended to cover ter-blockpolymers, tetra-blockpolymers and so on. In the context of the present invention, a polymer block has a molecular weight of at least 1,000. The molecular weights of the polymers referred to in this description are expressed in grams/mole.

Embodiments of the present invention relate to polymer matrices formed from gel-forming polymers such as block co-polymers comprising at least one rigid or hard block and at least one elastomeric or soft block.

Referring in more detail to the above, the gel-forming polymer preferably is a high molecular weight polymer imparting gelling properties to the composition for forming the polymer matrix. Essentially any polymer which will form a gel-based polymer matrix may be considered. Polymers from a wide variety of different polymer systems have been shown to provide good gelling properties. Representative of such diverse polymers are crystalline polymers such as ultrahigh molecular weight polyethylene (UHMWPE), polyethylene/acrylic acid copolymers, butyl methacrylate/acrylic acid copolymers, and thermoplastic block copolymer elastomers such as styrene tri-block copolymers. Thermoplastic block copolymer elastomers, which typically comprise at least one rigid block and at least one elastomeric block (and that are hydrophobic in nature) are particularly preferred.

In an embodiment, examples of the (at least one) rigid block comprise a polystyrene (PS) block or a poly(methylmethacrylate) (PMMA) block and/or the at least one elastomeric block is individually selected from hydrogenated or non-hydrogenated poly(butadiene) or hydrogenated or non-hydrogenated poly(isoprene). Hydrogenated poly(butadiene) is also known as poly(ethylene-butylene). Hydrogenated poly(isoprene) is also known as poly(ethylene-propylene).

It further has been found that gel forming block co-polymers including polystyrene or PMMA blocks are particularly suitable as they can be readily dissolved in organic solvents and form polymer matrices that have suitable $CO_2$-BOL retention properties. The particularly preferred polymers for the formulation of thermoplastic binders in accordance with the present invention are the tri-block styrene-ethylene/butylene-styrene copolymers. These elastomeric copolymers, commercially available under the trade-name Kraton® from Kraton Performance Polymers Inc., form particularly strong gels. Gelation of these polymers is considered to be by association of the styrene end blocks, due to their thermodynamic incompatibility with the rubber midblock in the polymer. Embodiments of some of these polymers are commercially available under the trade name Kraton®, e.g. Kraton G1650, Kraton G1651 and Kraton G1652, as provided by Kraton Performance Polymers, Inc.

Among the crystalline polymers exhibiting good gelling performance for thermoplastic binders, ultra-high molecular weight polymers are preferred. For hydrogen bonding polymers, polymer types comprising four or more reactive (hydrogen bond forming) functional groups per molecule are preferred.

In an embodiment, the block co-polymer has a weight-average molecular weight ($M_w$) in the range of 1,000-1,000,000, preferably in the range of 10,000-500,000. It has been found that if the gel-forming block co-polymer has a $M_w$ in this range, the polymer matrix can be readily formed using inkjet printing techniques whilst at the same time having favourable glass temperature characteristics.

As already disclosed by Heldebrandt et al. as well as by S. Stegmaier et al., for instance in Sensors and Actuators B: Chemical, 154(2), 2011, pages 270-276, many amidine or guanidine bases provide good sensitivity towards $CO_2$. Therefore, the appropriate base to be used in the $CO_2$ sensor of the IC of the present invention may be selected based on other desirable properties, e.g. sensor lifetime. For instance, the sensor lifetime may be negatively affected by relatively volatile amidine or guanidine bases evaporating from the polymer matrix, such that it may be desirable to select a base with a relatively high boiling point (or low vapour pressure in the operating temperature range of the IC).

In an embodiment, the amidine base is a liquid compound according to or comprising Formula I:

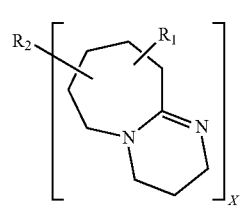

Formula I wherein $R_1$ and $R_2$ are individually selected from hydrogen, a linear or branched unsubstituted or substituted $C_1$-$C_{30}$ alkyl group, a linear or branched unsubstituted or substituted $C_1$-$C_{30}$ alkoxy group, a linear or branched unsubstituted or substituted $C_1$-$C_{30}$ thioalkoxy group, a $C_6$-$C_{12}$ unsubstituted or substituted aryl group or a linear or branched low molecular weight polymer molecule selected from hydrogenated or non-hydrogenated poly(butadiene) or hydrogenated or non-hydrogenated poly(isoprene). The molecular weight of these low molecular weight molecules is 300-10000, preferably between 1000-5000 and most preferably between 1500 and 3000 grams/mole.

X is an integer preferably selected from 1 to 10, more preferably selected from 1 to 4 and most preferably selected from 1 to 2. Molecules with X=1 will be referred to as mono-functional (containing 1 amidine or guanidine functional group per molecule). Molecules with X=2 will be referred to as di-functional (containing 2 amidine or guanidine functional groups per molecule. Molecules with X>2 will be referred to as polyfunctional (containing more than 2 amidine or guanidine functional groups) active molecules.

The $R_1$ and $R_2$ groups primarily have the function of tuning the volatility of the amidine base, and have no significant impact on the reactivity of the base in the presence of $CO_2$.

The organic alcohol preferably is a liquid, which is also preferred to have a high boiling point (i.e. low vapour pressure in the operating temperature range of the IC) for the same reasons as mentioned for the amidine or guanidine base. For this reason, the organic alcohol may be selected from the group comprising of $C_6$-$C_{30}$ linear, branched or cyclic alkyl alcohols and $C_6$-$C_{30}$ linear, branched or cyclic alkenyl alcohols comprising at least one carbon-carbon double bond, or a linear or branched low molecular weight polymer molecule selected from hydrogenated or non-hydrogenated poly(butadiene) or hydrogenated or non-hydrogenated poly(isoprene). The molecular weight of these low molecular weight molecules is 300-10000, preferably between 1000-5000 and most preferably between 1500 and 3000 grams/mole. Similarly to the $CO_2$ sensitive molecules, the alcohol can be mono- or polysubstituted (~R1 and ~R2 from the amidine molecules) and mono- or polyfunctional (containing one or several —OH groups per molecule).

In the context of the present invention, the term 'substituted' in relation to a chemical group of the polymer refers to the replacement of one or more of the hydrogens of such a chemical group with a substituent selected from a halogen (F, Cl, Br, or I), a hydroxyl group (—OH), an $C_{1-9}$ alkoxy group, a $C_{1-9}$ haloalkoxy group, an oxo (=O) group, a nitro group (—$NO_2$), a cyano group (—CN), an amino group (—$NH_2$), an azido group (—$N_3$), an amidino group (—C(=NH)$NH_2$), a hydrazino group (—$NHNH_2$), a hydrazono group (=N($NH_2$)), an aldehyde group (—C(=O)H), a sulfinic acid group (—S(=O)$_2$H), a carbamoyl group (—C(O)$NH_2$), a thiol group (—SH), a thiocyano group (—SCN), a tosyl group ($CH_3C_6H_4SO_2$—), a carboxylic $C_1$ to $C_6$ alkyl ester group (—C(=O)OR wherein R is a $C_1$ to $C_6$ alkyl group), a carboxyl group (—C(=O)OH), a carboxylic acid salt (—C(=O)OM) wherein M is an organic or inorganic anion, a sulfonic acid group (—$SO_3$H), a sulfonic monobasic salt (—$SO_3$M wherein M is an organic or inorganic cation), a phosphonic acid group (—$PO_3H_2$), a phosphonic acid mono- or dibasic salt (—$PO_3$MH or —$PO_3M_2$ wherein M is an organic or inorganic cation), a $C_1$ to $C_{20}$ alkyl group, a $C_2$ to $C_{16}$ alkenyl group, a $C_6$ to $C_{20}$ aryl group, a $C_6$ to $C_{20}$ aryloxy group, a $C_7$ to $C_{13}$ arylalkyl group, a $C_1$ to $C_4$ alkoxy group, a $C_1$ to $C_{20}$ heteroalkyl group, a $C_3$ to $C_{20}$ heteroarylalkyl group, a $C_3$ to $C_{20}$ cycloalkyl group, a $C_3$ to $C_{15}$ cycloalkenyl group, a $C_6$ to $C_{15}$ cycloalkynyl group, a $C_2$ to $C_{20}$ heterocycloalkyl group, and a combination thereof, instead of hydrogen, provided that the substituted atom's normal valence is not exceeded.

According to another aspect of the present invention, there is provided a composition for forming the polymer matrix of the integrated circuit of embodiments of the present invention, the composition comprising a volatile solvent; and a gel-forming polymer, an organic alcohol, and an organic amidine or guanidine base dissolved in said volatile solvent. In the context of the present invention, this composition will be further referred to as the "ink". This allows for the formation of the polymer matrix on the IC by the deposition of the ink on the electrodes of the IC, preferably by ink-jet printing, followed by the (rapid) evaporation of the volatile solvent such as toluene. In the context of the present invention, the resulting gel will be further referred to as the polymer gel, being a mix of a gel-forming polymer, an organic base and an alcohol. The gel is formed by physical crosslinking of the gel-forming block copolymer polymer such that the formation of the polymer matrix does not require an additional chemical reaction that could affect the amidine or guanidine base in the composition as previously explained.

In an embodiment, examples of the (at least one) rigid block comprise a polystyrene (PS) block or a poly(methylmethacrylate) (PMMA) block and/or the at least one elastomeric block is individually selected from hydrogenated or non-hydrogenated poly(butadiene) (PB) or hydrogenated or non-hydrogenated poly(isoprene) (PI). Hydrogenated poly (butadiene) is also known as poly(ethylene-butylene) (PEB). Hydrogenated poly(isoprene) is also known as poly(ethylene-propylene) (PEP). Particularly suitable gel-forming block copolymers may be selected from PS-PEB, PS-PEB-PS and PS-PI-PS. Embodiments of some of these polymers are commercially available under the trade name Kraton®, e.g. Kraton G1650, Kraton G1651 and Kraton G1652, as provided by Kraton Performance Polymers, Inc.

In an embodiment, the total amount of solutes (gel-forming block co-polymer, alcohol and amidine or guanidine base) is 0.1 to 25% in the ink (said solution), to match the deposition requirements. The gel-forming block co-polymer is present in a range of 40-70% by weight in the final deposit (=relative to the total weight of the solutes). It has been found that if the fraction of the polymer in the total amount of solutes is less than 40%, the deposit formed following the evaporation of the volatile solvent may not jellify and therefore remain liquid and spread beyond desirable boundaries on the IC. In contrast, if the weight fraction of the polymer in the total amount of solutes is more than 70%, the responsiveness of the $CO_2$ sensor is reduced after forming the polymer matrix.

Suitable organic solvents include but are not limited to toluene, xylene and tetrahydrofuran.

The selection of the high molecular weight polymer to be used in formulating the ink for forming the polymer gel is governed primarily by the solubility or miscibility of the selected polymer in the solvents used to form the composition and the gelling characteristics thereof as the solvent is evaporated to form the polymer matrix.

Each of these properties, including the gelling characteristics of the polymers may readily be determined by routine experiment. A solution of the candidate polymer, the alcohol and the amidine or guanidine base in a suitable solvent such as toluene, xylene or THF is prepared and the solubility or miscibility of the polymer, the alcohol and the amidine or guanidine base in the solvent is determined. The solvent is then evaporated and the presence or absence of gelling is noted. Examples of polymers evaluated in this way which have demonstrated poor gelling behaviour include polystyrene based block co-polymers having hydrophilic elastomeric blocks.

According to yet another aspect of the present invention, there is provided a method of manufacturing an integrated circuit according to embodiments of the present invention, the method comprising providing a semiconductor substrate carrying a plurality of circuit elements; and forming a $CO_2$ sensor over said substrate by forming a pair of electrodes over the semiconductor substrate; depositing a droplet of the ink according to an embodiment of the present invention over said electrodes; and evaporating the volatile solvent from said droplet to form said polymer gel.

In a preferred embodiment, the integrated circuit further comprises at least one patterned metallization layer for interconnecting the plurality of circuit elements and a passivation layer over the at least one patterned metallization layer, wherein each electrode of the pair of electrodes is at least partially located on the passivation layer and conductively coupled to respective portions of the at least one patterned metallization layer. This allows for the $CO_2$-sensor to be integrated in the backend of the IC manufacturing process, such that the other circuit elements of the IC are protected from the process steps required to manufacture the sensor, and has the further advantage that high temperature steps, e.g. implant activation, have already been completed such that materials may be used that would otherwise be unsuitable due to their inability to withstand such elevated temperatures.

Preferably, the method further comprises forming at least one patterned metallization layer for interconnecting said circuit elements over said semiconductor substrate; and forming a passivation layer over said at least one patterned metallization layer, wherein said $CO_2$ sensor is formed on the passivation layer. The embodiments of the method of the present invention facilitate a cost-effective integration of a $CO_2$ sensor having ppm sensitivity on (the metallization stack of) an IC.

It has been found that the sensitivity of the $CO_2$-sensor on the IC of the present invention can be affected by significant changes in the relative humidity to which the IC is exposed. This may be addressed by the inclusion of a relative humidity sensor to cross-reference the output of the $CO_2$-sensor.

BRIEF DESCRIPTION OF THE EMBODIMENTS

Figure 3:
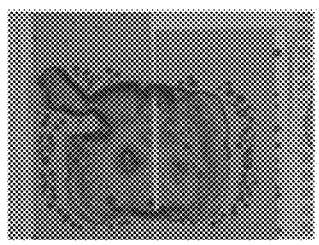
Figure 3:
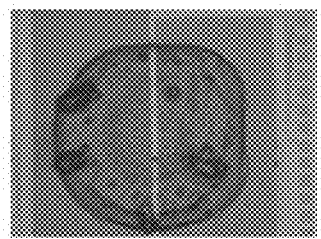
Figure 3:
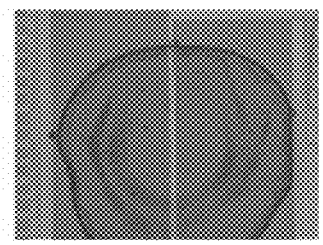
Figure 3:
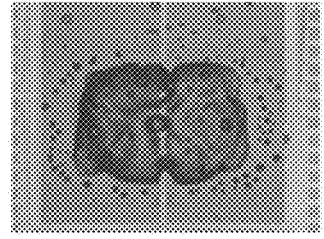
Figure 3:
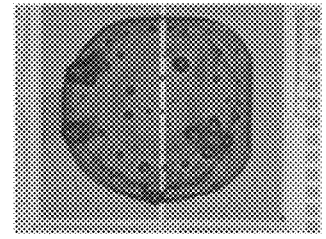
Figure 4:
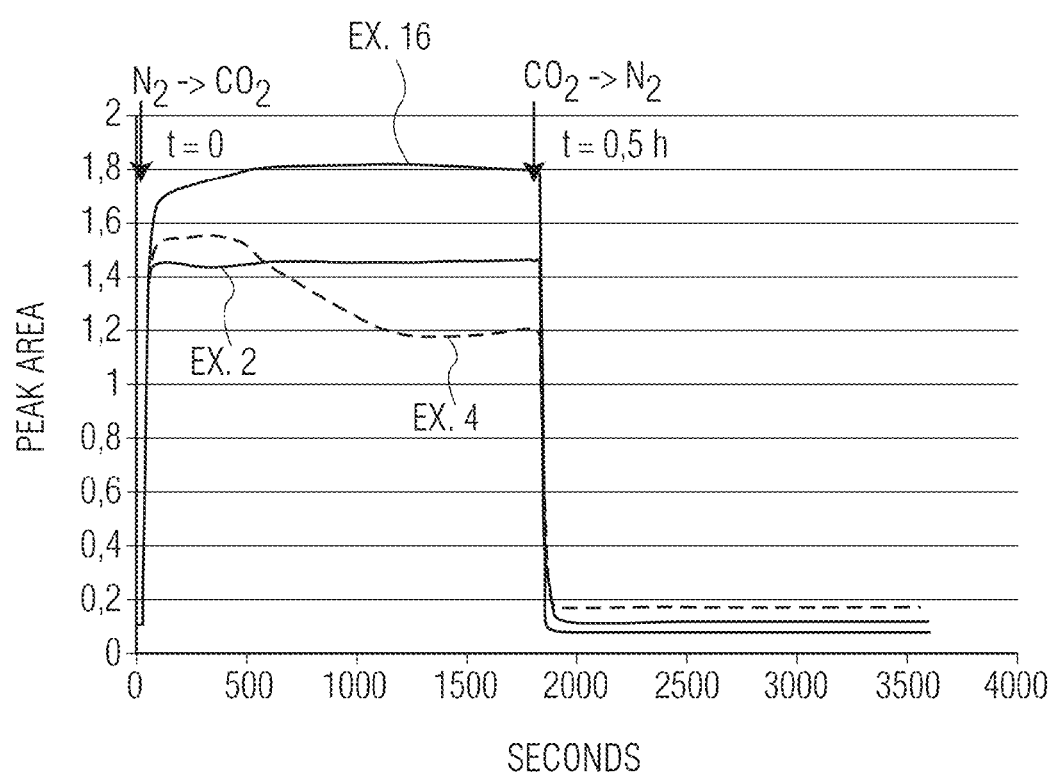
Figure 5:
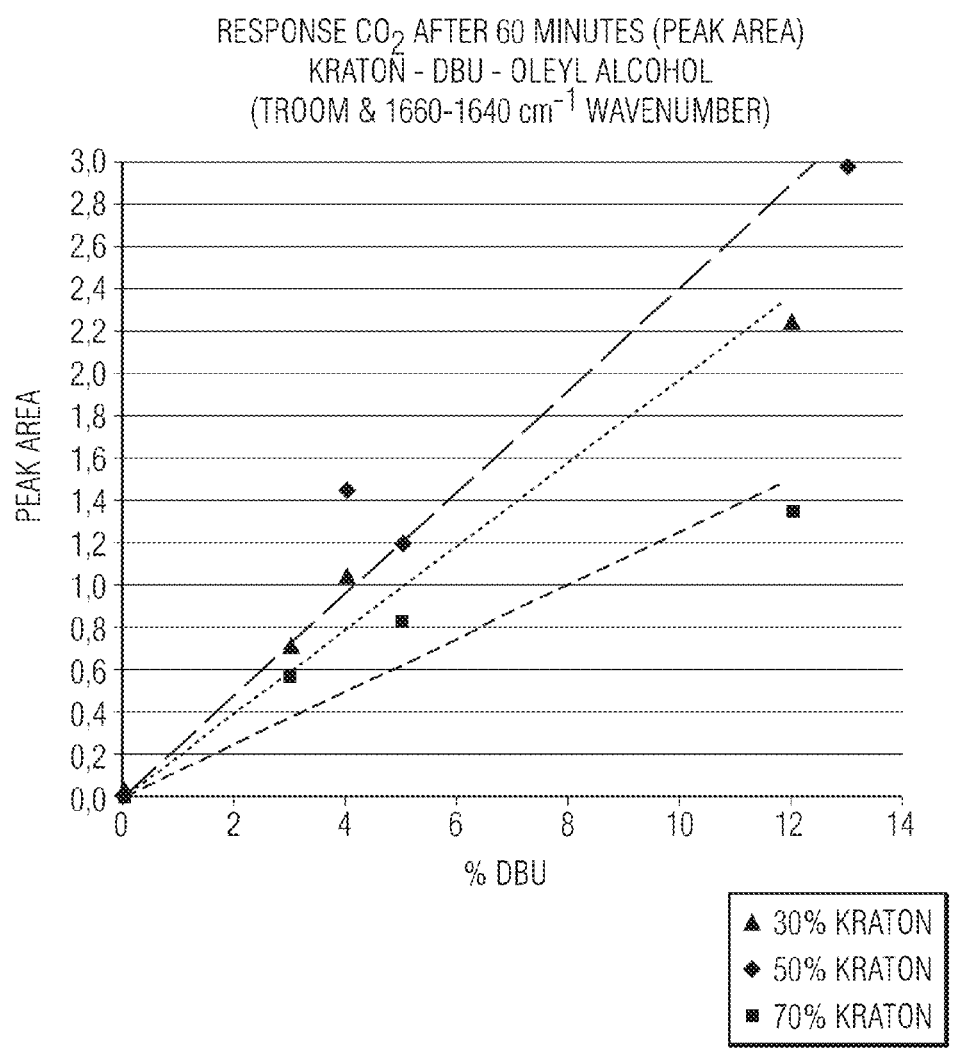
Figure 6:
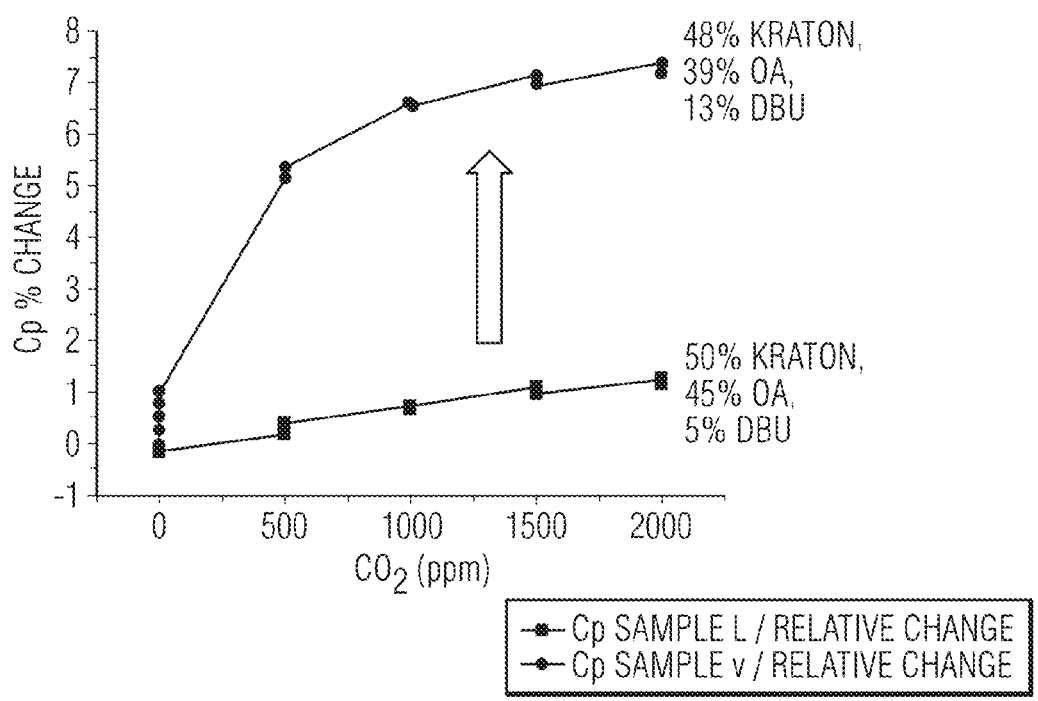
Figure 7:
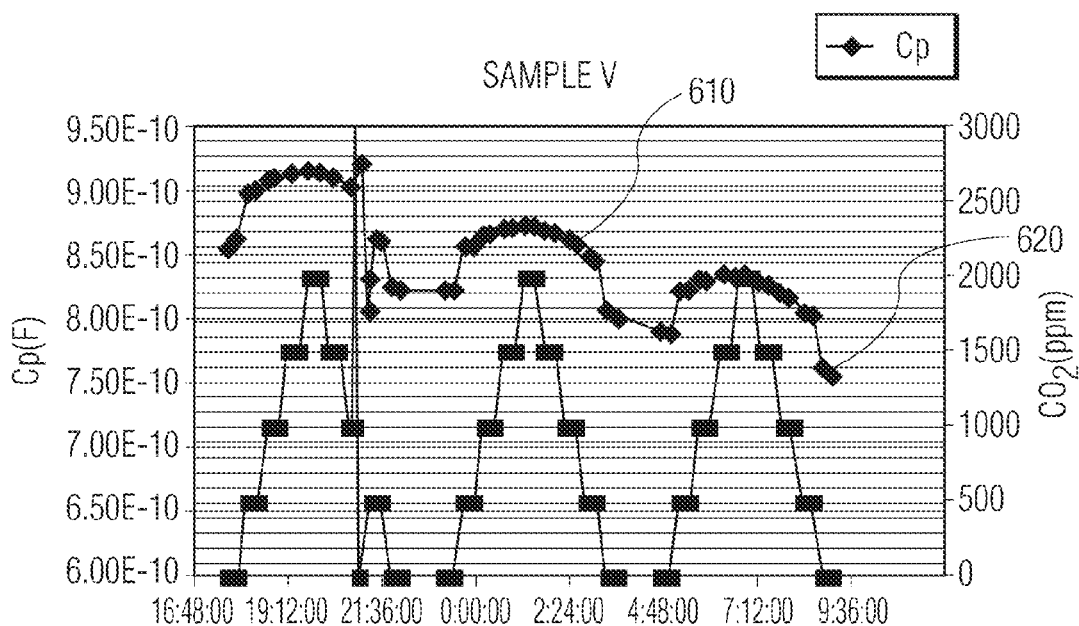
Figure 8:
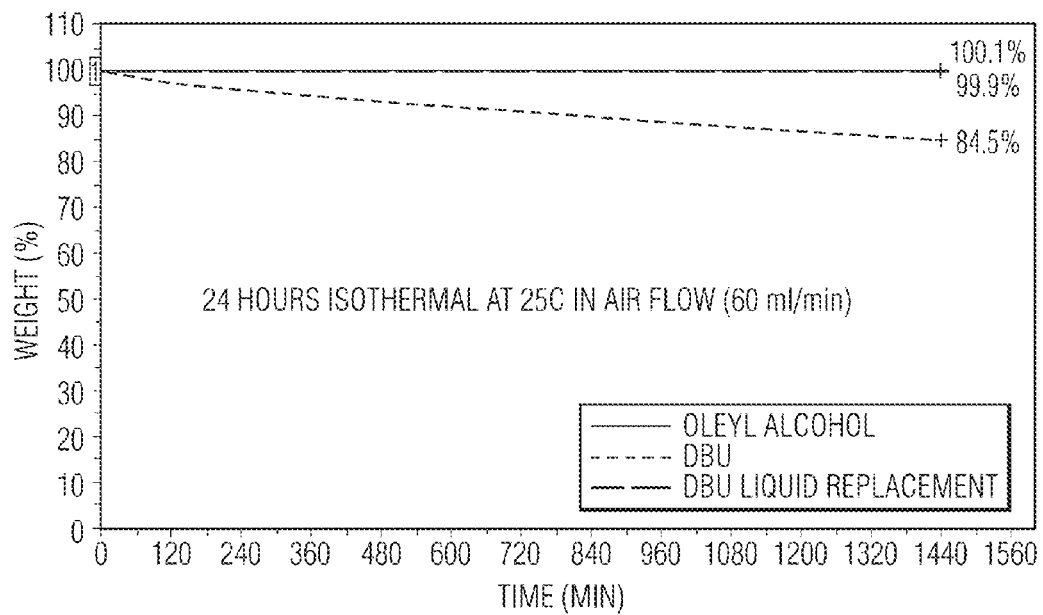
Figure 9:
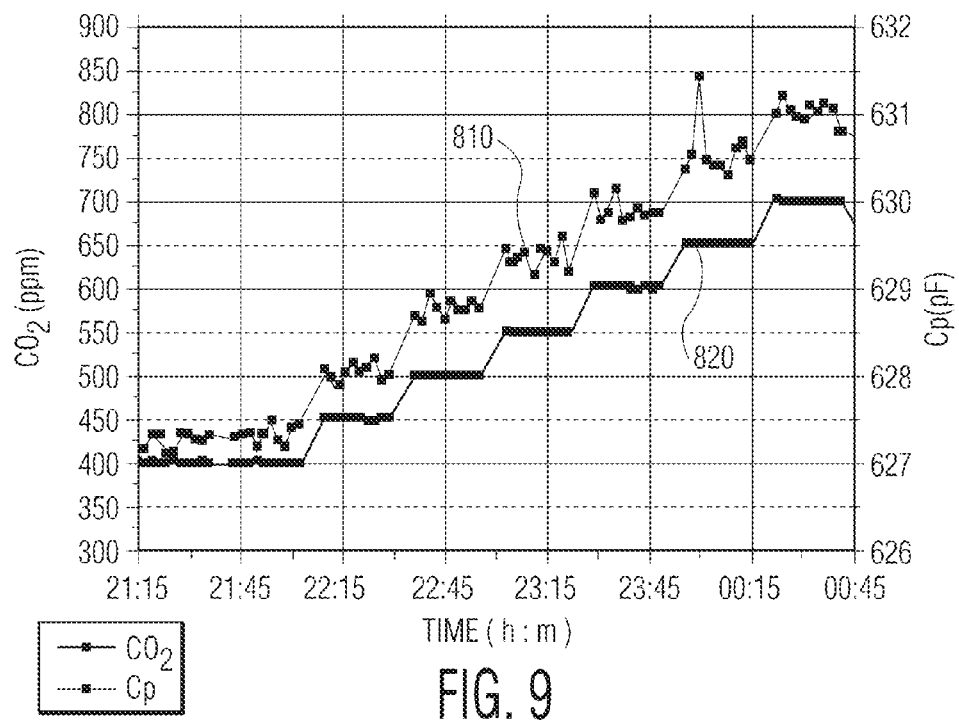

Embodiments of the invention are described in more detail and by way of non-limiting examples with reference to the accompanying drawings, wherein:

FIG. 1 schematically depicts an example embodiment of an IC of the present invention;

FIG. 2A-2I schematically depict an example embodiment of a method of manufacturing an IC of the present invention;

FIG. 3 schematically depicts the flow characteristics of a deposited droplet of a composition according to an embodiment of the present invention as a function of polymer content;

FIG. 4 schematically depicts FT-IR data indicating the sensitivity to $CO_2$ of a $CO_2$ sensor on an IC according to an embodiment of the present invention as a function of different polymer matrices;

FIG. 5 schematically depicts the sensitivity to $CO_2$ of a $CO_2$ sensor on an IC according to an embodiment of the present invention as a function of the amount of polymer and $CO_2$-BOL in a composition for forming such a $CO_2$ sensor;

FIG. 6 schematically depicts the dependence of the sensitivity to $CO_2$ of a $CO_2$ sensor on an IC according to an embodiment of the present invention to changes in the composition from which the $CO_2$-BOLS is immobilized on the IC;

FIG. 7 schematically depicts the sensitivity to $CO_2$ of a $CO_2$ sensor on an IC according to an embodiment of the present invention;

FIG. 8 schematically depicts a time-dependent component to the sensitivity to $CO_2$ of a $CO_2$ sensor on an IC according to an embodiment of the present invention;

FIG. 9 schematically depicts the sensitivity to $CO_2$ of a $CO_2$ sensor on an IC according to another embodiment of the present invention; and FIG. 10A-10D schematically depicts the sensitivity to $CO_2$ of a $CO_2$ sensor on an IC according to another embodiment of the present invention as a function of relative humidity.

DETAILED DESCRIPTION OF THE DRAWINGS

It should be understood that the Figures are merely schematic and are not drawn to scale. It should also be understood that the same reference numerals are used throughout the Figures to indicate the same or similar parts.

FIG. 1 schematically depicts an embodiment of an IC 100 of the present invention comprising a semiconductor substrate 110 such as a Si, SiGe, silicon on insulator (SOI), GaAs, or GaN heterojunction substrate, and so on, which typically carries a plurality of circuit elements 111. In addition, the substrate 110 further carries a $CO_2$ sensor 120 including a first electrode 122 laterally separated from a second electrode 124. The electrodes may be made of any suitable conductive material, although materials that are routinely available in an existing IC process flow are preferable to limit cost. For example, aluminium may be used in a CMOS process for the electrodes 122 and 124.

The electrodes 120 and 122 may be formed in any suitable spatial configuration. In a particularly advantageous embodiment, the first electrode 120 and the second electrode 122 are interdigitated comb electrodes as such an electrode lay-out ensures a electrode large surface area, and consequently a large capacitor plate area, which therefore yields a very sensitive pressure sensor as the sensitivity tends to scale with plate area.

The $CO_2$ sensor 120 may be electrically insulated from the substrate 110 by an electrically insulating layer 112, e.g. a passivation layer. Any suitable material or combinations of such materials, e.g. $SiO_2$, $Si_3N_4$, low-k dielectric materials and so on may be used for the electrically insulating layer 112.

In an embodiment, conductive portions 116, e.g. vias, may connect the electrodes 122 and 124 to respective circuit elements 111 for operating the $CO_2$ sensor 120. In an alternative embodiment, the electrodes 122 and 124 may be connected to respective external contacts such that the $CO_2$ sensor 120 may be operated separate to the IC 100 using external equipment.

The $CO_2$ sensitivity of the $CO_2$ sensor 120 is provided by a $CO_2$-BOL 126 that is kept over the electrodes 122 and 124, i.e. immobilized, by a polymer matrix 128. The $CO_2$-BOL 126 typically comprises an organic alcohol and an organic amidine or guanidine base in the presence of a trace or catalytic amount of water that is necessary to provide the sensor 120 with its $CO_2$-sensitivity. Various aspects of the $CO_2$-BOL 126 and the polymer matrix 128 will be explained in more detail later.

In an embodiment, the first electrode 122 and the second electrode 124 form the plates of a capacitor of the $CO_2$ sensor 120 in case of a capacitive $CO_2$ sensor 120. In this embodiment, a change in the dielectric constant of the $CO_2$-BOL 126 resulting from the reaction of the liquid with $CO_2$ is measured, e.g. by the application of an alternating current to the electrodes 122 and 124, in which case the capacitance difference between first electrode 122 and second electrode 124 may be measured in a differential fashion, e.g. using a sigma/delta capacitance to digital converter.

Alternatively, the $CO_2$ sensor may be a resistive $CO_2$ sensor in which case the electrodes 122 and 124 are arranged to provide a direct current or a voltage across the $CO_2$-BOL 126 to measure the changes in the electric resistivity of the $CO_2$-BOL as a result of the reaction of the liquid with $CO_2$.

Although the pressure sensor may be manufactured on any suitable part of the semiconductor substrate 110, it is preferred that the sensor is located on the metallization stack of the IC 100. Typically, an IC 100 comprises one or more patterned metallization layers separated from each other by one or more electrically insulating material layers with different metal layers interconnected through the one or more electrically insulating material layers using vias. This is well-known per se and will therefore not been explained in more detail for the sake of brevity. It is merely pointed out that the exact nature of the metallization is outside the scope of the present invention and that any suitable material for forming such a metallization stack may therefore be contemplated.

It is furthermore noted that although not explicitly shown in FIG. 1, the IC 100 may comprise other sensors that are additional to the $CO_2$ sensor 120. In particular, the IC 100 may further comprise a relative humidity sensor to cross-reference the output of the $CO_2$ sensor 120 as will be explained in more detail later. The integration of relative humidity sensors on an IC 100 including in the backend process of such an IC is well-known per se; see for instance EP 24 20 826 A1, such that the manufacture and the operating principle of such a relative humidity sensor will not be explained in further detail for the sake of brevity only.

Figure 2A:
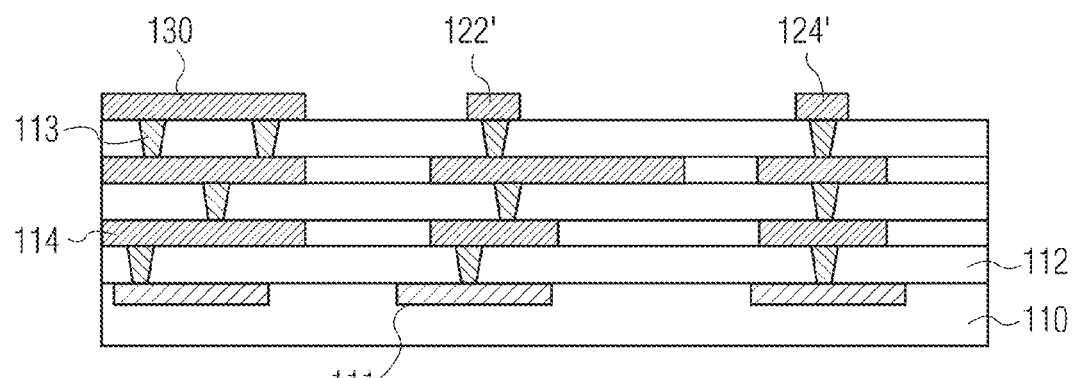

An example embodiment of the manufacture of such a $CO_2$-sensor in the backend of an IC manufacturing process, i.e. on top of the metallization, is shown in FIG. 2A. It should be understood that this process flow is just one of many possible approaches that may be chosen for such a manufacturing process and that may alternatives, e.g. the interchange or omission of selected process steps will be apparent to the skilled person.

The method commences in step in FIG. 2A with the provision of a semiconductor substrate 110 carrying a plurality of circuit elements 111, e.g. transistors, diodes and so on, onto which a metallization stack comprising at least one patterned metal layer 114 and an electrically insulating layer 112 is formed, with conductive interconnections through the dielectric layer(s) being provided by vias 113. Any suitable number of metal layers 112 and dielectric layers 114 may be present. The upper metal layer may comprise any suitable number of bond pads 130 as well as metal portions 122' and 124' for conductively coupling the appropriate circuit elements 111 to the electrodes 122 and 124 in case of a $CO_2$ sensor 120 being operated by circuit elements 111 of the IC 100.

Metal portions in different patterned metal layers 114 may be conductively interconnected by one or more vias 113 formed in a dielectric layer 112 in between the respective portions of the patterned metal layers 114. Any suitable material may be used to form the metallization stack, such as Ti, TiN, Al, Cu and combinations thereof to define the metal layers 114 and silicon oxide, silicon nitride, low-k dielectrics and other dielectric materials as well as combinations thereof to form the dielectric layers 112. Although in FIG. 2A these layers are depicted as single layers, it should be understood that these layers themselves may comprise a stack of layers, as is common design practice in contemporary semiconductor technologies such as sub-micron CMOS technologies.

Figure 2B:
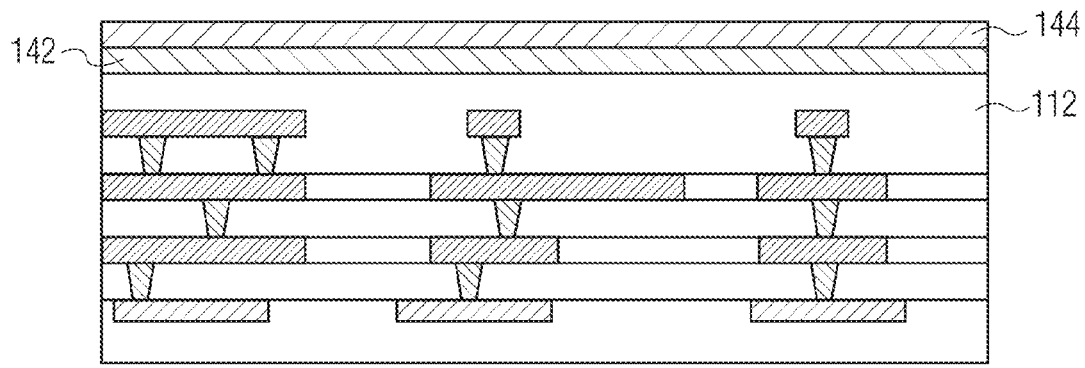

A passivation stack comprising one or more dielectric layers is formed over the metallization stack. In FIG. 2B, the passivation stack comprises a silicon nitride layer 144 and a silicon oxide layer 142 by way of non-limiting example only. Such layers may be formed in any suitable manner to any suitable thickness. By way of non-limiting example only, the silicon nitride layer 144 may be formed in a plasma-enhanced chemical vapour deposition (PE-CVD) step to a thickness of approximately 600 nm and the silicon oxide layer 142 may be formed to a thickness of approximately 100 nm using a high-density plasma oxidation step in a 140 nm CMOS process. In an embodiment, the deposition of the silicon oxide layer 142 may also be used to form an upper dielectric layer 112 over the upper metallization layer of the metallization stack.

A planarization step such as a chemical mechanical polishing (CMP) step may be applied to planarize the silicon nitride layer 144 if necessary. This is not shown for the sake of brevity only. It will be obvious to the skilled person that different layer thicknesses and different materials may be used for the planarization stack depending on process technology and requirements. For instance, the silicon nitride layer 144 may be a silicon-rich SiN layer, as this material has a good selectivity towards HF vapour-based etch recipes and resists polymer formation during such an etching step.

Figure 2C:
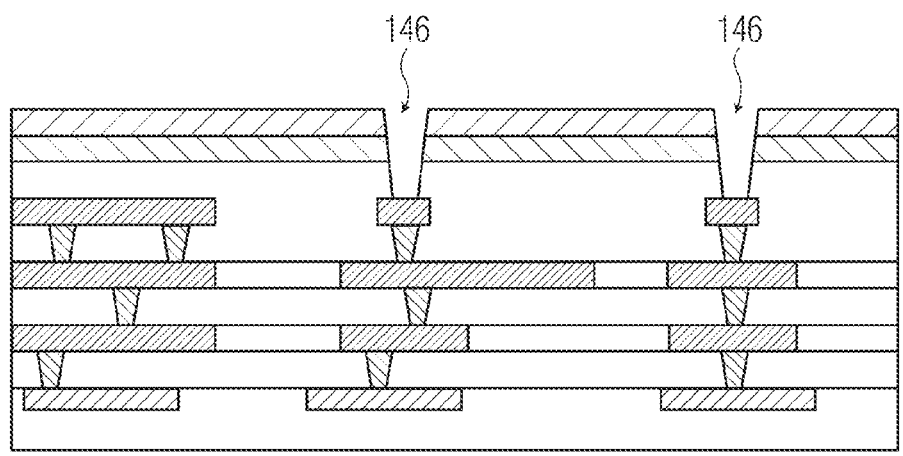

In the step shown in FIG. 2C, trenches 146 are formed through the passivation stack layers 142 and 144 using one or more suitable etch recipes to provide access to the electrode contacts 122' and 124' in the upper metallization layer 114. A suitable diameter of the trenches 146 in a 140 nm CMOS process is 700 nm although different dimensions will obviously be appropriate for different scale technologies. In an alternative embodiment (not shown), trenches may also be formed to expose the bond pads 130 at the same time. The trenches 146 may be defined using any suitable mask, e.g. a hard mask or a photolithographic mask, as is well known per se to the skilled person.

Figure 2D:
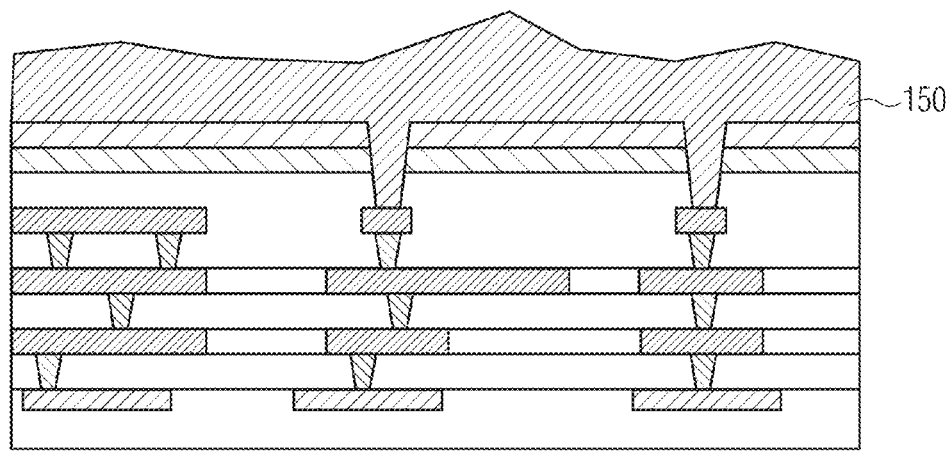
Figure 2E:
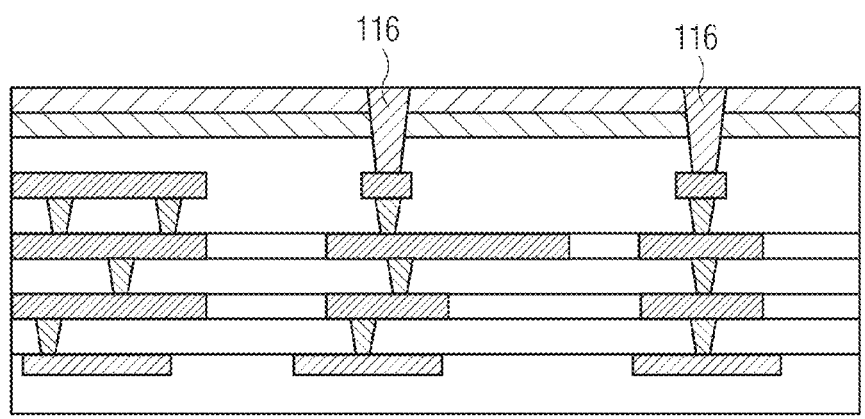

Next, the trenches 146 are filled with a conductive material 150, e.g. tungsten, using any suitable deposition process such as chemical vapour deposition (CVD) in the step shown in FIG. 2D, to form conductive portions, e.g. vias 116 to the electrode contacts 122' and 124', and to the bond pads 130 if applicable, through the passivation stack defined by dielectric layers 142 and 144 in the step shown in FIG. 2E by the removal of access conductive material 150, e.g. by applying a planarization step, e.g. a CMP step, on the upper passivation layer 144. The steps shown in FIG. 2D and FIG. 2E may be omitted if the $CO_2$ sensor on the IC is to be externally controlled, as previously explained.

Figure 2F:
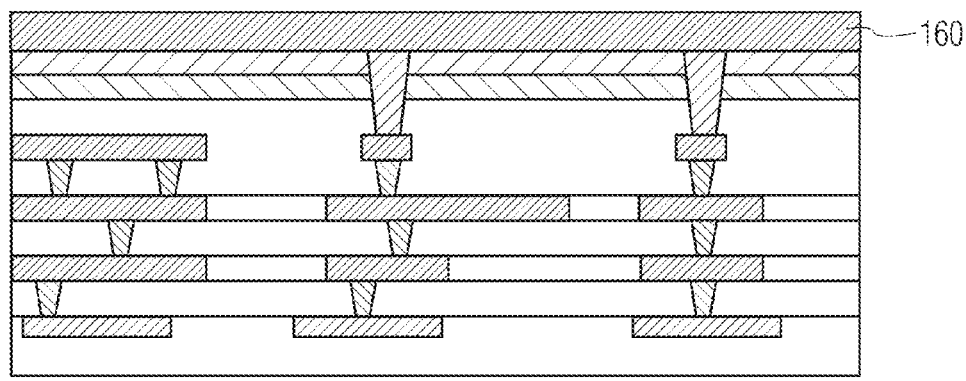
Figure 2G:
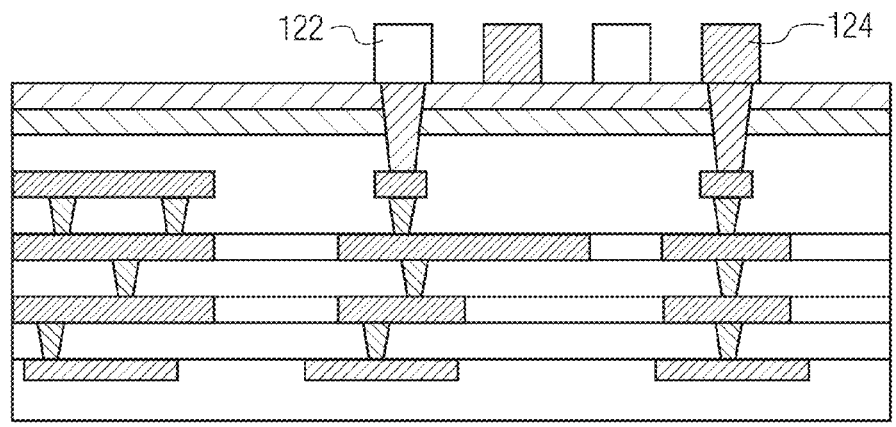

In the step shown in FIG. 2F, a suitable metal layer 160 is deposited and subsequently patterned in the step shown in FIG. 2G using any suitable mask to form the first electrode 122 and the second electrode 122, and bond pad contacts if applicable. A non-limiting example of a suitable metal is aluminum, which is routinely available in a CMOS process, e.g. a 140 nm CMOS process. However, it will be understood that any suitable metal may be used, which preferably is a metal that is readily available in the chosen technology in which the IC 100 is manufactured.

Figure 2H:
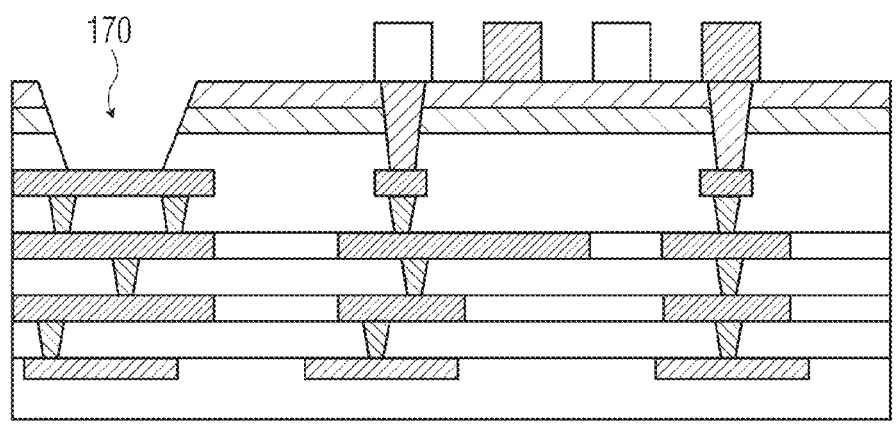

In an optional step shown in FIG. 2H, the passivation stack may be opened to provide access to the one or more bond pads 130 in case no bond pad contacts have been formed on the passivation stack as previously explained. This may be done in any suitable manner. As the selective opening of a passivation stack is well-known per se, this will not be explained in further detail for the sake of brevity only.

Figure 2I:
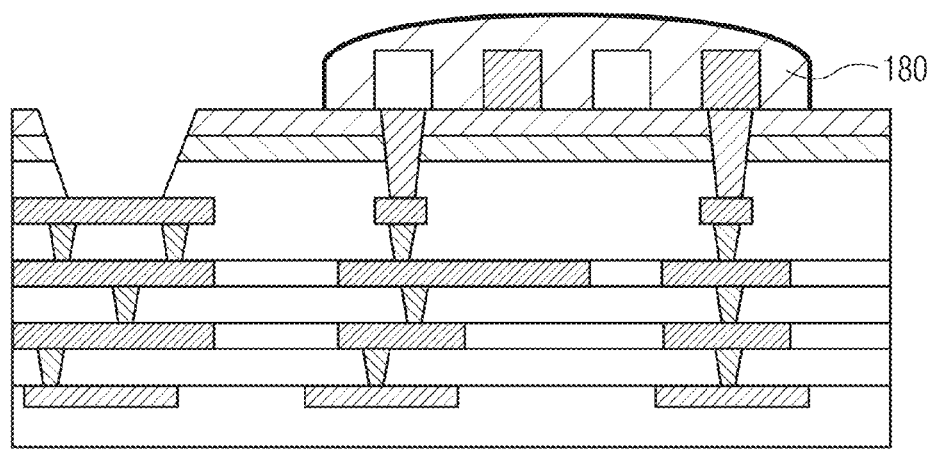

In the step shown in FIG. 2I a volume, e.g. one or more droplets, of a composition 180 including a volatile solvent and the $CO_2$-BOL 126 dissolved in said volatile solvent together with a precursor of the polymer matrix 128, e.g. a dissolved polymer or polymer precursor, is deposited on the electrodes 122 and 124, e.g. using pipetting or inkjet printing after which the volatile solvent is evaporated from the composition 180 to form the polymer matrix 128 that traps the $CO_2$-BOL 126 over the electrodes 122 and 124. The polymer matrix 128 is formed by physical gelation, for instance using a physically cross-linking block co-polymer with hydrophobic elastomeric blocks that has been dissolved in the composition 180, thus reducing the risk that the chemical composition of the $CO_2$-BOL 126 is negatively affected during the formation of the polymer matrix 128 because no chemical reaction is required to form the polymer matrix 128. The IC 100 may subsequently be finalized using any suitable processing steps.

As previously mentioned, particularly suitable materials for forming the polymer matrix 128 are polymers that aggregate or gelate according to a mechanism sometimes referred to as physical crosslinking, thereby forming multiple domains, in particular a first domain of relatively high structural rigidity, which defines the boundaries or walls of a second domain in which materials can be encapsulated. Polymers that are known to exhibit such properties include semi-crystalline polymers, hydrogen-bonding polymers and polymers comprising two or more blocks of different polymers or oligomers, including at least one rigid block and at least one elastomeric block, which preferably is hydrophobic. Such polymers will be referred to as block copolymers in the present application. The different blocks of the copolymers are typically selected to respectively provide the aforementioned first and second domains.

In an embodiment, the polymer matrix 128 is predominantly formed from a gel-forming block co-polymer that comprises at least one hard or rigid block, e.g., a PS block or a PMMA block and at least one soft block, i.e., an elastomeric block, which preferably is hydrophobic in nature. It has been found that in particular PS-based and PMMA-based block co-polymers combine several advantageous properties including good solubility in organic solvents that can be used in inkjet printing processes such as toluene, xylene and THF, and stable physical crosslinking such that stable (micellar) micro-domains are formed by the hydrophobic elastomers in which the $CO_2$-BOL can be retained for periods of time that allow extended use of the $CO_2$-sensor 120 on the IC 100.

Particularly suitable soft or elastomeric blocks include hydrogenated or non-hydrogenated poly(butadiene) (PB) or hydrogenated or non-hydrogenated poly(isoprene) (PI). Hydrogenated poly(butadiene) is also referred to as poly(ethylene-butylene) (PEB). Hydrogenated poly(isoprene) is also referred to as poly(ethylene-propylene) (PEP).

Particularly suitable gel-forming block copolymers include PS-PEB (also known as SEB), PS-PEB-PS (also known as SEBS), PS-PI-PS (also known as SIS).

It is for instance known that styrene-butadiene-styrene (SBS) and styrene-(ethylene-butylene)-styrene (SEBS) block co-polymers are capable of physical crosslinking, i.e. of gel formation without requiring chemical reaction. Such polymers are commercially available under the trade name Kraton®, e.g. Kraton G1650, Kraton G1651 and Kraton G1652, as provided by Kraton Performance Polymers, Inc.

When choosing the polymer for forming the polymer matrix 128, the weight percentage of the polymer is preferably chosen in the range of 40-70 wt %, based on the combined weight of the components of the $CO_2$-BOL 126 and the polymer. It has been found that if the weight of the polymer is chosen below 40 wt %, the polymer gel is not strong enough to prevent the droplet of the composition 180 to spread over the IC 100 upon exposing the IC 100 to vibrations. If the weight percentage of the polymer is above 70 wt %, the $CO_2$-sensor 120 may not be sensitive enough.

To be able to process (e.g. inkjet-print or micropipetting) the ink, the ink viscosity of said ink should be tuned to match the deposition requirements. This can be done by choosing the right temperature, solvent, the concentration of the block co-polymer in said solvent and the molecular weight of the block co-polymer, or adding processing aids.

The specific composition of the $CO_2$-BOL 126, i.e. the organic alcohol and the amidine or guanidine base, is not particularly critical to the present invention. Any suitable $CO_2$-BOL may be used. Specifically, any amidine or guanidine base capable of reversibly reacting with $CO_2$ (see reaction scheme I below) may be contemplated.

Reaction Scheme I

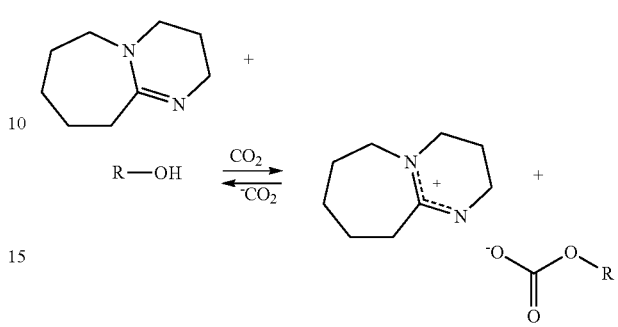

Similarly, any organic alcohol capable of participating in this reversible reaction may be contemplated. The selection of the $CO_2$-BOL 126 can be based on the following design considerations. For ease of manufacturing, the ink to be deposited onto the first electrode 122 and the second electrode 124 ideally has a viscosity tuned to facilitate this deposition, e.g. by ink-jet printing, drop casting, spin coating or the like. At the same time, the components of the $CO_2$-BOL 126 ideally should have a negligible vapour pressure in the operating temperature range of the $CO_2$-sensor 120 to ensure that the sensitivity of the sensor is not significantly reduced over time by substantial evaporation of the base and/or the organic alcohol components of the $CO_2$-BOL 126 from the polymer matrix 128.

In an embodiment, the volatility of e.g. the amidine base may be decreased by the introduction of at least one substituent as shown in Formula I:

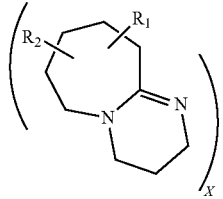

Formula I wherein $R_1$ and $R_2$ are individually selected from hydrogen, a linear or branched unsubstituted or substituted $C_1$-$C_{30}$ alkyl group, a linear or branched unsubstituted or substituted $C_1$-$C_{30}$ alkoxy group, a linear or branched unsubstituted or substituted $C_1$-$C_{30}$ thioalkoxy group, a $C_6$-$C_{12}$ unsubstituted or substituted aryl group or a linear or branched low molecular weight polymer molecule selected from hydrogenated or non-hydrogenated poly(butadiene) or hydrogenated or non-hydrogenated poly(isoprene). The molecular weight of these low molecular weight molecules is 300-10000, preferably between 1000-5000 and most preferably between 1500 and 3000 grams/mole.

X is an integer preferably selected from 1 to 10, more preferably selected from 1 to 4 and most preferably selected from 1 to 2. Molecules with X=1 will be referred to as mono-functional (containing 1 amidine or guanidine functional group per molecule). Molecules with X=2 will be referred to as di-functional (containing 2 amidine or guanidine functional groups per molecule. Molecules with X>2 will be referred to as polyfunctional (containing more than 2 amidine or guanidine functional groups) active molecules.

In other words, the introduction of one or more of such substituents can be used to tune the viscosity and vapour pressure of the base, e.g. the amidine base. In particular, longer substituent chains and/or branched substituent chains tend to increase the viscosity and vapour pressure of organic compounds such as the base, e.g. the amidine base, of the $CO_2$-BOL 126.

The same principle applies to the organic alcohol of the $CO_2$-BOL 126. The organic alcohol may be selected from the group comprising of $C_6$-$C_{30}$ linear, branched or cyclic alkyl alcohols and $C_6$-$C_{30}$ linear, branched or cyclic alkenyl alcohols comprising at least one carbon-carbon double bond, or a linear or branched low molecular weight polymer molecule with alcohol end groups, selected from hydrogenated or non-hydrogenated poly(butadiene) or hydrogenated or non-hydrogenated poly(isoprene). The molecular weight of these low molecular weight molecules is 300-10000, preferably between 1000-5000 and most preferably between 1500 and 3000 grams/mole. Similarly to the amidine base, the alcohol may contain multiple alcohol groups per molecule.

By selecting the length and degree of branching of the alkyl or alkenyl chains and selection of the number of alcohol groups or indeed other substituents, the viscosity and vapour pressure of the organic alcohol of the $CO_2$-BOL 126 may be tuned.

The viscosity of the ink may further be tuned by controlling the weight-average weight $M_w$ of the block co-polymer that is to form the polymer matrix 128 in the composition. A block co-polymer with a relatively low $M_w$, e.g. $M_w \approx 1,000$ has favourable viscosity properties but may have a relatively low $T_g$, which can limit the temperature range in which the $CO_2$-sensor 120 is operable. A block co-polymer with a relatively high $M_w$, e.g. $M_w \approx 1,000,000$ may have glass temperature $T_g$ properties but may have a relatively high viscosity, which may make the deposition of the composition on the electrodes 122, 124 more cumbersome.

In an embodiment, the composition of the present invention may comprise a relatively low-$M_w$ block co-polymer e.g. $M_w < 10,000$. The $T_g$ of the resulting polymer matrix may be relatively low. To increase the glass temperature $T_g$ of the resulting polymer matrix 128 for instance, up to 50 wt % of the total weight of the polymer fraction in the composition may be formed of one or more polymers exhibiting a higher $T_g$ that are miscible with the rigid block, and not miscible with the soft block of the relatively low-$M_w$ block co-polymer, e.g. up to 50 wt % high molecular weight polystyrene and/or polyphenyl ether with a weight-average molecular weight $M_w$ of up to 250,000 may be mixed with the relatively low-$M_w$ block co-polymer. The resulting polymer matrix 128 is a blend of the hydrophobic block co-polymer and the further polymer. It is for instance known per se that Kraton polymers may be successfully mixed with such polymers to form such blends; see e.g. Mazard C., Benyahia L. & Tassin J-F; Dynamic mechanical properties of polystyrene-based block copolymers blended with poly (2,6-dimethyl-1,4-phenylene oxide), Polymer International 52, 514-521 (2003).

Alternatively, the glass temperature of the relatively low-$M_w$ block co-polymer may be increased by tuning the rigid blocks of the relatively low-$M_w$ block co-polymer or by co-polymerizing the rigid blocks.

In an embodiment, the weight average molecular weight or number average molecular weight of the hard blocks such as the polystyrene blocks is at least 2,000 or even at least 4,000, and may be selected from the range of 1,000-1,000, 000. It has been found that when the hard blocks have a weight selected within this range a block co-polymer is obtained that can be readily dissolved in volatile solvents that facilitate the deposition of the composition on a target substrate, e.g. by means of printing processes such as ink jet printing, whilst at the same time readily forming a gel, i.e. physically cross-linked matrix after deposition, as will be demonstrated by the examples below.

The present invention will now be explained in more detail by the following examples. It should be understood that these examples are not intended to limit the scope of the present invention and that the skilled person will readily understand that embodiments not specifically detailed in the following examples may also be contemplated.

EXAMPLES

All amidines (except C24DBU, formula IV, and GI1000DBU, formula V) alcohols and solvents were purchased from Sigma Aldrich and used as purchased. C24DBU and GI1000DBU were obtained from SyMOChem B.V. All Kraton polymers were obtained from Kraton Performance Polymers Inc. All other polymers were supplied by Polymer Source Inc. GI1000 alcohol was supplied by Nisso Chemicals Europe GmbH.

Example 1

A polymer gel with a composition comprising 50 wt % Kraton G1652, 10 wt % amidine of Formula II (DBU) and 40 wt % oleyl alcohol (cis-9-octadecen-1-ol) was formed. The PS blocks in Kraton G1652 have a weight-average molecular weight Mw of 9,100 and the elastomeric (hydrogenated ethylene-butylene) blocks in Kraton G1652 have a weight-average molecular weight Mw of 42,500. These components were dissolved in toluene to form an ink. The total weight fraction of the components was 5 wt % in toluene. A droplet of the ink was deposited on a wafer using a Microdrop printer with a 100 micron nozzle and the toluene was subsequently evaporated to form the polymer gel on the wafer.

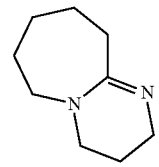

Formula II

DBU 1,8-Diazabicyclo[5.4.0]undec-7-ene

Example 2

An ink comprising 70 wt % Kraton G1652, 10 wt % DBU and 20 wt % oleyl alcohol in toluene was formed. The total weight fraction of the components was 5 wt % in toluene. A droplet of the ink was deposited on a wafer using a Microdrop printer with a 100 micron nozzle and the toluene was subsequently evaporated to leave a polymer gel on the glass plate.

Example 3

An ink to produce a polymer gel as in Example 1 was formed using a PS-pI-PS triblock co-polymer (Kraton D1114) instead of Kraton G1652. Kraton D1114 has a weight-average molecular weight of about 160,000 and a styrene content of 19 wt %. A droplet of the ink was deposited on a wafer using a Microdrop printer with a 100 micron nozzle and the toluene was subsequently evaporated to leave a polymer gel on the glass plate.

Example 4

An ink to produce a polymer gel as in Example 1 was formed using an amidine according to Formula III (DiBut) instead of DBU. A droplet of the ink was deposited on a wafer using a Microdrop printer with a 100 micron nozzle and the toluene was subsequently evaporated to leave a polymer gel on the glass plate.

Formula III

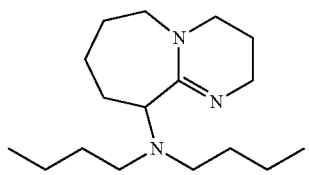

DiBut (6-(Dibutylamino)-1,8-diazabicyclo[5.4.0]undec-7-ene)

Example 5

An ink to produce a polymer gel as in Example 1 was formed using an alcohol according to Formula IV (C24OH) instead of oleyl alcohol. A droplet of the ink was deposited on a wafer using a Microdrop printer with a 100 micron nozzle and the toluene was subsequently evaporated to leave a polymer gel on the glass plate.

Formula IV

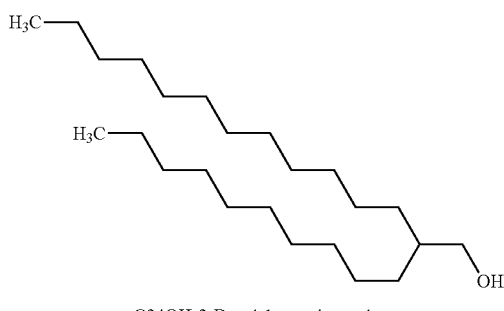

C24OH-2-Decyl-1-tetradecanol

Example 6

An ink to produce a polymer gel as in Example 1 was formed using an amidine according to Formula V (C24DBU) instead of DBU. A droplet of the ink was deposited on a wafer using a Microdrop printer with a 100 micron nozzle and the toluene was subsequently evaporated to leave a polymer gel on the glass plate.

Formula V

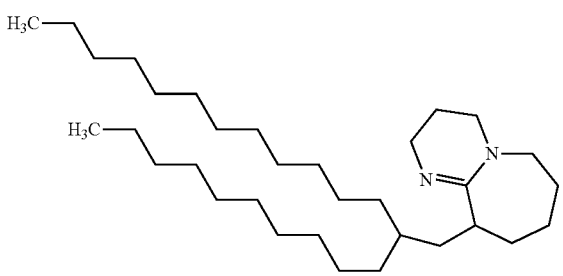

Example 7

An ink to produce a polymer gel as in Example 2 was formed using an amidine according to Formula VI (GI1000DBU) instead of DiBut. GI1000DBU is a random co-polymer (i.e. n and m in Formula VI are not exactly determined) having a measured $M_w$ of around 4,500. A droplet of the ink was deposited on a wafer using a Microdrop printer with a 100 micron nozzle and the toluene was subsequently evaporated to leave a polymer gel on the glass plate.

Formula VI

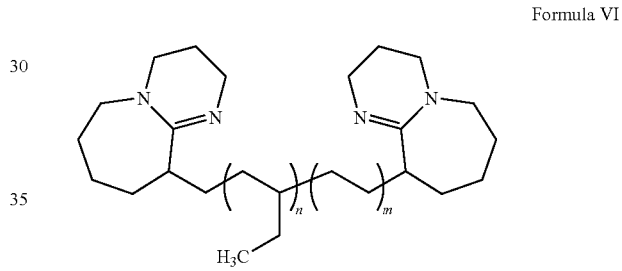

Example 8

An ink to produce a polymer gel as in Example 1 was formed using Kraton G1651 obtained from Kraton Performance Polymers Inc., instead of Kraton G1652. The PS blocks in Kraton G1651 have a weight-average molecular weight Mw of 39,000 and the elastomeric (hydrogenated ethylene-butylene) blocks in Kraton G1652 have a weight-average molecular weight Mw of 182,000. A droplet of the ink was deposited on a wafer using a pipette and the toluene was subsequently evaporated to leave a polymer gel on the wafer.

Comparative Example 1

A polymer gel with a composition comprising 30 wt % Kraton G1652 obtained from Kraton Performance Polymers Inc., 10 wt % amidine of Formula III (DBU) and 60 wt % oleyl alcohol was formed. These components were dissolved in toluene to form an ink. The total weight fraction of the components in the ink was 5 wt % in toluene. A droplet of the ink was deposited on a wafer using a Microdrop inkjet printer with a 100 micron nozzle after which the toluene was evaporated to form the (soft) polymer gel on the wafer.

Comparative Example 2

A polymer gel as in Example 1 was formed using a PS-pDMS block co-polymer purchased from Polymer Source Inc instead of Kraton G1652. The PS blocks in this polymer have a number average molecular weight $M_n$ of 34,000 and the pDMS blocks have a number average molecular weight $M_n$ of 12,800. A droplet of the ink was deposited on a wafer using a Microdrop printer with a 100 micron nozzle and the toluene was subsequently evaporated. The presence of a liquid on the wafer after evaporation of the solvent indicated the failure to form a polymer gel from this composition.

Comparative Example 3

An ink to produce a polymer gel as in Example 1 was formed using a PS-pDMS-PS triblock co-polymer purchased from Polymer Source Inc. instead of Kraton G1652. The PS blocks in this polymer have a number average molecular weight $M_n$ of 8,000 and the pDMS blocks have a number average molecular weight $M_n$ of 36,000. A droplet of the ink was deposited on a wafer using a Microdrop printer with a 100 micron nozzle and the toluene was subsequently evaporated. The presence of a liquid on the wafer after evaporation of the solvent indicated the failure to form a polymer gel from this composition.

Comparative Example 4

An ink to produce a polymer gel as in Example 1 was formed using a PS-pEO block co-polymer purchased from Polymer Source Inc. instead of Kraton G1652. The PS blocks in this polymer have a number average molecular weight Mn of 6,100 and the pDMS blocks have a number average molecular weight Mn of 46,900. The polymer was dissolved in the toluene after heating. A droplet of the ink was deposited on a wafer using a Microdrop printer with a 100 micron nozzle and the toluene was subsequently evaporated. The presence of a liquid on the wafer after evaporation of the solvent indicated the failure to form a polymer gel from this composition.

Comparative Example 5

An ink to produce a polymer gel as in Example 1 was formed using a pEO-PS-pEO block co-polymer obtained from Polymer Source Inc. instead of Kraton G1652, with number average molecular weights ($M_e$) of 7,500 for the PEO blocks and 4,100 for the PS block. The polymer was dissolved in the toluene after heating. A droplet of the ink was deposited on a wafer using a Microdrop printer with a 100 micron nozzle and the toluene was subsequently evaporated to leave a translucent polymer matrix on the wafer. The presence of a liquid on the wafer after evaporation of the solvent indicated the failure to form a polymer gel from this composition.

Comparative Example 6

A PS-p4VP block co-polymer was obtained from Polymer Source Inc. with a number average molecular weight Mn of 56,300 of the PS blocks and 43,500 of the P4VP blocks. This polymer could not be dissolved in toluene or THF.

FIG. 3 depicts photographs of droplets of the compositions formed in Examples 1-2 and Comparative Example 1 after pipetting onto a wafer (top row) and after exposing the pipetted droplets to a mechanical stability test, having the samples strongly vibrated for at least 30 minutes (bottom row). It can be seen that spreading of the droplet takes place for a composition having 30 wt % Kraton G1652 as the polymer matrix, whereas such behaviour is not observed at 50 wt % and 70 wt % Kraton contents.

It has been found that in particular the triblock co-polymers give polymer matrix films having excellent gel forming characteristics. The gel forming characteristics are further improved by using relatively high weight rigid blocks such as polystyrene blocks in the physically cross-linking hydrophobic block co-polymers and by using alcohols and bases that have as high as possible viscosity without significantly compromising the deposition techniques of the compositions.

FT-IR Experiments

FT-IR (Fourier transform infrared spectroscopy) is used as a screening method to determine whether ions are formed during reaction with $CO_2$.

The polymer matrices of Examples 1-8 were all applied on a diamond ATR crystal and subjected to a stream of $CO_2$ followed by a stream of $N_2$. A Biorad FTS6000 spectrometer, equipped with a MCT detector was used to collect spectra. FT-IR spectra of each polymer matrix were taken before, during and after the exposure to $CO_2$ and $N_2$ respectively. In all cases, upon exposure of the polymer matrix to $CO_2$, the FT-IR spectra demonstrated an IR absorption in the 1660-1640 $cm^{-1}$ region indicative of the C—O stretch vibration of the carbonate anion and the protonation of the N—C=N amidine bond:

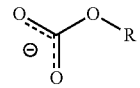

After flushing with $N_2$, this IR absorption disappeared in all FT-IR spectra, thus indicating the reversible nature of the reaction between $CO_2$ and the $CO_2$-BOL 126.

An example response is shown in FIG. 4, which depicts the area of the absorption in the range of 1660-1640 $cm^{-1}$ of the polymer matrix of example 1, 3 and 8 as a function of the exposure of the matrix to $CO_2$ and $N_2$. The reversibility of the $CO_2$-binding reaction is clearly demonstrated. It is noted that the variation in the area of the absorption in the range of 1660-1640 $cm^{-1}$ for example 3 was caused by a fluctuation in the $CO_2$ supply, thus also indicating that these polymer matrices can be used for the quantitative detection of $CO_2$.

Further compositions were investigated using FT-IR absorption spectroscopy, wherein the polymer matrices formed from these compositions were exposed to a $CO_2$ flow until saturation of the absorption peak at 1660-1640 $cm^1$ was observed. The results are shown in Table I.

TABLE I

| | Kraton 1652 (wt %) | DBU (wt %) | Oleyl alcohol (wt %) | Area of 1660-1640 $cm^{-1}$ absorption (arbitrary units) |
|---|---|---|---|---|
| Example 9 | 70 | 3 | 27 | 6 |
| Example 10 | 70 | 5 | 25 | 9 |
| Example 11 | 68 | 12 | 20 | 8 |
| Example 12 | 50 | 5 | 45 | 10 |
| Example 13 | 48 | 4 | 48 | 15 |
| Example 14 | 48 | 13 | 39 | 28 |
| Example 15 | 30 | 3 | 67 | 8 |
| Example 16 | 30 | 4 | 66 | 11 |
| Example 17 | 29 | 12 | 59 | 23 |
| Comparative | 70 | 0 | 30 | 0 |

TABLE I-continued

| | Kraton 1652 (wt %) | DBU (wt %) | Oleyl alcohol (wt %) | Area of 1660-1640 cm$^{-1}$ absorption (arbitrary units) |
|---|---|---|---|---|
| Example 7 Comparative Example 8 | 30 | 0 | 70 | 0 |
| Comparative Example 9 | 0 | 0 | 100 | 0 |
| Comparative Example 10 | 0 | 100 | 0 | 2 |

Examples 9-17 all produced measurable FT-IR signals for the $CO_2$ bound to the DBU. These results further show that a particular good reactivity can be achieved for an amidine fraction of 4 wt % or more at a block co-polymer weight fraction not exceeding 50 wt %. It is believed that at higher weight fractions the polymer matrix 120 is less permeable such that it is more difficult for the $CO_2$ to reach the $CO_2$-BOL 126 in the matrix although this still results in a sufficiently strong measurable signal. Table I also clearly demonstrates that the absorption at 1660-1640 cm$^{-1}$ can only be attributed to the reaction product of Reaction Scheme I as for the comparative examples 7-10 in which at least one of the components of the $CO_2$-BOL 126 is absent, no absorption at 1660-1640 cm$^{-1}$ could be detected.

In a further experiment, the amidine content in Examples 1-2 and Comparative Example 1 was systematically varied to investigate the $CO_2$ sensitivity of the $CO_2$ sensor 120 at T=25° C. The results are shown in FIG. 5, in which the sensitivity is derived from the peak area of an absorption peak at 1660-1640 cm$^{-1}$ in the FT-IR spectrum of the composition. A clear correlation with the polymer content was observed. An increase in sensitivity was observed when increasing the Kraton content from 30 wt % to 50 wt %, whereas a decrease in sensitivity was observed for a Kraton content of 70 wt %, which as previously explained is attributed to the polymer matrix becoming less permeable at higher weight percentages, such that the $CO_2$ cannot penetrate the polymer matrix as easily as at lower weight percentages.

Consequently, the weight percentage of a gel forming polymer, e.g. Kraton, in the composition 180 is preferably chosen in the range of 40-70 wt % based on the combined weight of the components of the $CO_2$-BOL 126 and the polymer to avoid spreading problems below this range and significantly decreased sensitivity above this range.

With regards to $CO_2$ sensitivity, the choice and amount of amidine or guanidine base and organic alcohol in the $CO_2$-BOL 126 is not particularly critical. It has already been disclosed by Heldebrandt et al. that a large number of amidine or guanidine bases are suitable for the binding of $CO_2$ in such a liquid. For instance, the combined weight fraction of the amidine or guanidine base and organic alcohol may be up to 60 wt % of the total weight of the components forming the polymer gel 120, wherein the amidine or guanidine base for instance may be chosen in a range of 5-45 wt % and the organic alcohol for instance may be chosen in a range of 15-55 wt %.

Capacitive Measurements

The influence of the amounts of these components has been tested by the present inventors by the exposure of a capacitive $CO_2$ sensor on a metallization stack of a CMOS IC manufactured in a 140 nm technology to different levels of $CO_2$ at T=25° C., in which different amounts of Kraton G1652 were used as the polymer matrix, different amounts of DBU were used as the amidine base and different amounts of oleyl alcohol were used as the organic alcohol.

The results are shown in FIG. 6. For a composition 180 comprising 50 wt % Kraton G1652, 45 wt % oleyl alcohol and 5 wt % DBU, a distinct increase in the capacitance of the $CO_2$ sensor 120 was detected at a $CO_2$ exposure as low as 500 ppm, whereas for a polymer gel 180 comprising 48 wt % Kraton G1652, 39 wt % oleyl alcohol and 13 wt % DBU, the sensitivity further increased by a factor ~50, with a noticeable increase of capacitance for $CO_2$ levels as low as 10 ppm.

It has been found that the choice of the constituents of the $CO_2$-BOL 126 can affect the lifetime of the $CO_2$ sensor, as relatively volatile constituents may slowly evaporate from the polymer matrix 128, thus reducing the sensitivity of the $CO_2$ sensor 120 over time. This is demonstrated in FIG. 7, which depicts the time-dependent changes in the measured capacitance 610 of a $CO_2$ sensor 120 including a polymer gel according to Example 1 and exposed to an atmosphere in which the $CO_2$ content 620 was periodically varied from 0-2,000 ppm by 500 ppm increments at T=25° C. As can be seen from FIG. 7, after 12 hours, about a 10% reduction in the overall capacitance change occurred.

To investigate the potential cause of this decrease, the $CO_2$-BOL 126 used in the above sensor was exposed to an air flow for 24 hours at T=25° C. The results are shown in FIG. 8, which clearly demonstrates the gradual evaporation of the DBU from the $CO_2$-BOL 126.

Hence, when choosing the amidine or guanidine base and the organic alcohol, preferably compounds should be chosen that have a high boiling point or at least a negligible vapour pressure at the desired operating temperature of the $CO_2$ sensor 120. This is particularly relevant if the sensor is to be used for prolonged periods of time, e.g. many weeks. In case of an amidine or guanidine base (or organic alcohol) that slowly evaporates from the sensor 120, the IC 100 may be calibrated using a time-dependent evaporation model such that the measured capacitance at a given point in time can be accurately correlated to a $CO_2$ concentration using the evaporation model.

It has been found that in particular individual combinations of the alcohols and bases of Formula II-VI yield embodiments of a $CO_2$-BOL 126 that have excellent lifetime characteristics. Obviously, any other suitable non-volatile alcohol and/or amidine or guanidine base may be used instead as the exact composition of these constituents of the $CO_2$-BOL 126 are not critical to the desired functionality of this liquid, as previously explained.

This is for instance demonstrated by FIG. 9, which depicts the change in capacitance of a $CO_2$ sensor 120 on an IC 100 formed from a composition according to Example 4. The sensor was exposed to 50 ppm increments of $CO_2$ over a 3.5 hour period at T=25° C. The measured change in capacitance is shown as transient 810 and the change in $CO_2$ concentration is shown as transient 820.

The sensor displayed a measurable sensitivity towards $CO_2$ levels well below 500 ppm, with no degradation of the sensitivity over the measured time period, thus clearly indicating that the higher boiling point of DiBut compared to DBU significantly increases the lifetime of the $CO_2$-sensor. Further improvements in lifetime were observed for $CO_2$-sensors manufactured using the compositions of Examples 5-7, which clearly indicates that the higher molecular weight components of the $CO_2$-BOL 126 increase the lifetime of the $CO_2$-sensor 120 as such higher molecular weight components have a reduced vapour pressure at the operating temperatures of the $CO_2$-sensor 120.

Figure 10A:
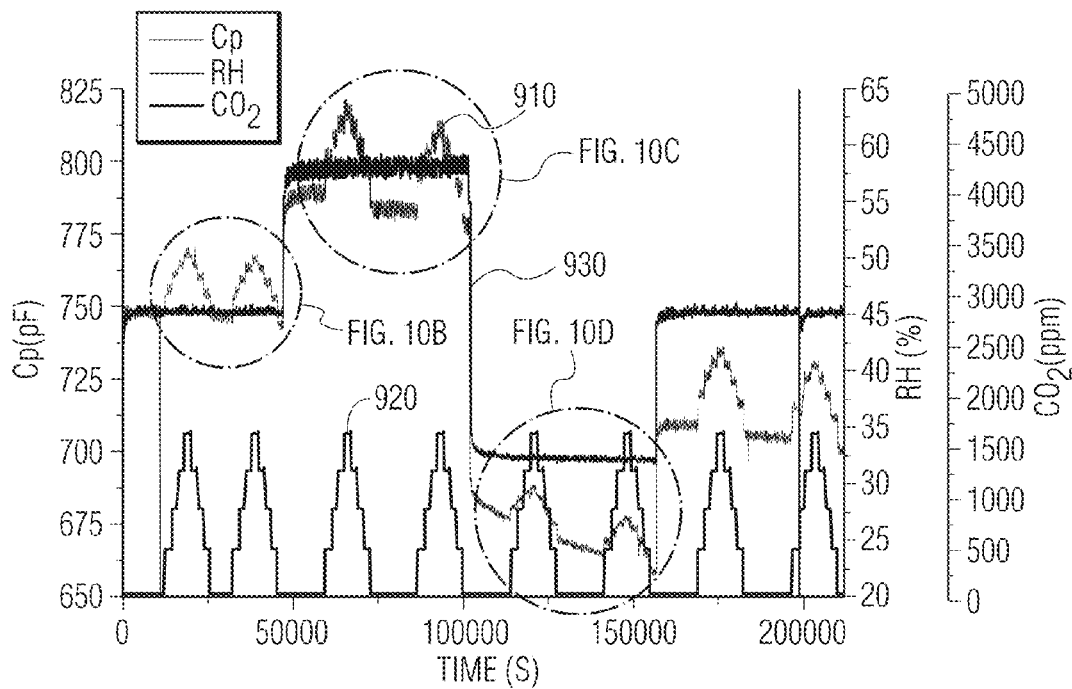
Figure 10B:
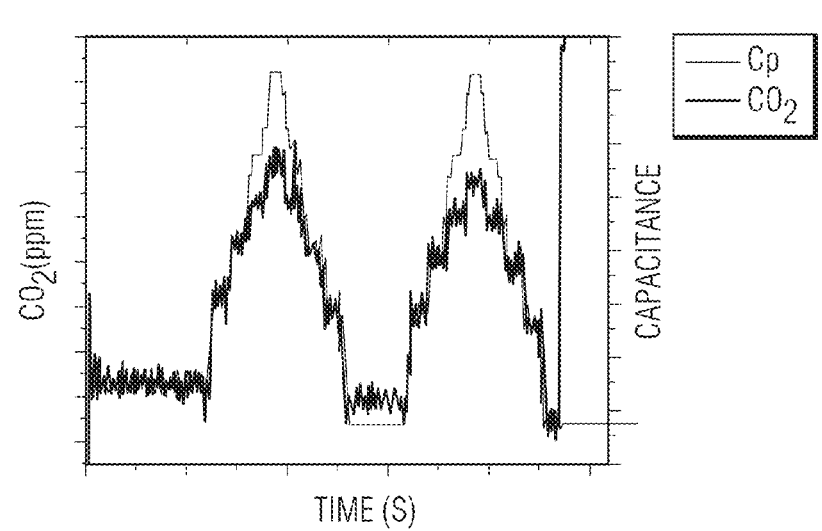
Figure 10C:
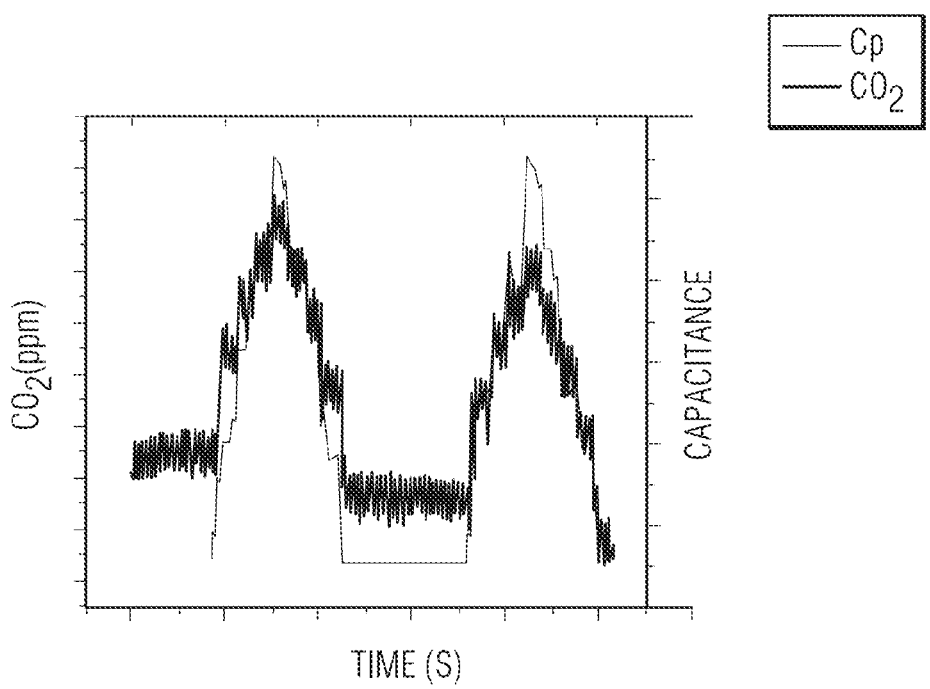
Figure 10D:
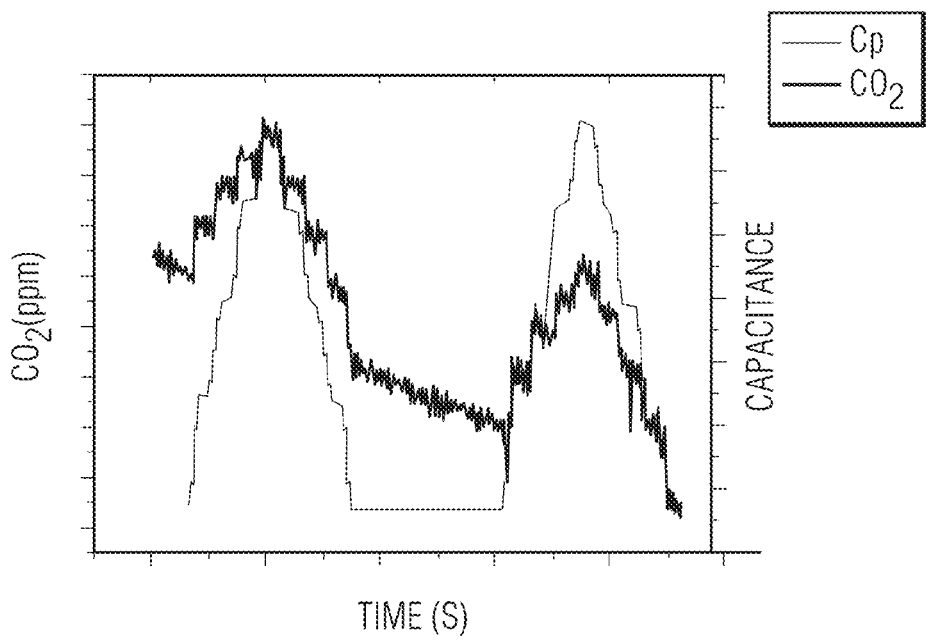

When the above CO₂ sensor based on the composition of Example 4 was exposed to different levels of CO₂ at different levels of relative humidity at T=25° C., it was found that the sensitivity of the CO₂ sensor showed some dependence of the relative humidity. This is shown in FIGS. 10A-10D. Transient 910 displays the measured change in capacitance, transient 920 displays the applied CO₂ levels and transient 930 displays the applied relative humidity (RH) level. It will be immediately apparent that there is a striking correlation between the RH level and the response of the sensor 120, as shown in FIGS. 10B-10D, with the sensor 120 losing linearity of response at low RH levels, i.e. below 35%.

The same behaviour was observed for the CO₂-sensors based on the compositions of Examples 2 and 5. For this reason, in an embodiment of the present invention the IC 100 further comprises a relative humidity sensor such that the output of the CO₂ sensor 120 can be correlated to the relative humidity determined using the relative humidity sensor in order to accurately quantify the CO₂ level determined by the CO₂-sensor 120. To this end, the IC 100 may comprise a signal processor that is arranged to interpret the respective output signals of the CO₂-sensor 120 and the relative humidity sensor, and which derives the actual CO₂ level from these two signals. As such cross-referencing principles are well-known per se, this will not be explained in further detail for the sake of brevity only.

The relative humidity sensor may be omitted if the IC 100 is to be used for qualitative detection of CO₂ only, e.g. in protective atmosphere food packaging where the detection of any amount of CO₂ can signal the degradation of the packaged food item.

It is furthermore noted that the amidine and guanidine bases have a distinct temperature range in which they display CO₂ sensitivity, at least when applied in a CO₂ sensor 120 of the IC 100 of the present invention. For instance, DBU (the compound of Formula II) and Dibut (the compound of Formula III) display good sensitivity to CO₂ in an operating window of T=0-40° C. Different CO₂-BOLs may be considered if different operating windows are required.

Finally, it is noted that although the above examples focus on PS as the hard block of choice, it is reasonable to expect that other hard blocks that are known per se to form a gel using the indicated amounts of alcohols and amidine or guanidine bases may be used instead. For instance, it is known from e.g. Yu et al. in Polymer (1997) Vol. 38, pages 2143-2154 that PMMA-based hydrophobic block co-polymers also exhibit physical cross-linking behaviour. Such polymers are for instance disclosed in U.S. Pat. No. 6,329,480.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An integrated circuit comprising:
    a semiconductor substrate carrying a plurality of circuit elements; and
    a CO₂-sensor over the semiconductor substrate, the sensor comprising:
        a pair of electrodes laterally separated from each other; and
        a CO₂-permeable polymer matrix at least partially covering the pair of electrodes,
    the CO₂-permeable polymer matrix immobilizing and encapsulating a CO₂-binding organic liquid comprising:
        an organic alcohol; and
        an amidine or guanidine base,
        wherein the dielectric constant of the liquid changes as a function of CO₂ concentration, and
        wherein the CO₂-permeable polymer matrix comprises a gel forming polymer.

2. The integrated circuit of claim 1, wherein the gel forming polymer is a block copolymer comprising at least one rigid block and at least one elastomeric block.

3. The integrated circuit of claim 2, wherein the at least one rigid block is individually selected from polystyrene (PS) and poly(methylmethacrylate) (PMMA), and/or
    wherein at least one elastomeric block is individually selected from hydrogenated or non-hydrogenated poly (butadiene) (PEB; PB) or hydrogenated or non-hydrogenated poly(isoprene) (PEP; PI).

4. The integrated circuit of claim 3, wherein the block copolymer is selected from PS-PEB, PS-PEB-PS and PS-PI-PS.

5. The integrated circuit of claim 2, wherein the block copolymer has a weight-average molecular weight (Mw) in the range of 1,000-1,000,000 and preferably in the range of 10,000-500,000.

6. The integrated circuit of claim 1, wherein the amidine base is a liquid compound according to or comprising Formula I:

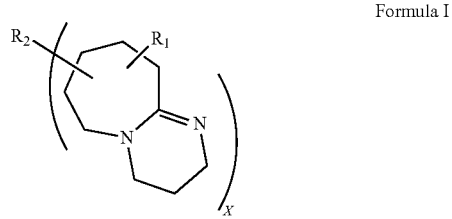

Formula I wherein R₁ and R₂ are individually selected from hydrogen, a linear or branched unsubstituted or substituted $C_1$-$C_{30}$ alkyl group, a linear or branched unsubstituted or substituted $C_1$-$C_{30}$ alkoxy group, a linear or branched unsubstituted or substituted $C_1$-$C_{30}$ thioalkoxy group, a $C_6$-$C_{12}$ unsubstituted or substituted aryl group or a linear or branched low molecular weight polymer molecule selected from hydrogenated or non-hydrogenated poly(butadiene) or hydrogenated or non-hydrogenated poly(isoprene), wherein X is an integer preferably selected from 1 to 10, more preferably selected from 1 to 4 and most preferably selected from 1 to 2, and wherein the molecular weight of the amidine base is 300-10000, preferably between 1000-5000 and most preferably between 1500 and 3000 grams/mole.

7. The integrated circuit of claim 1, wherein the organic alcohol is a liquid selected from the group comprising of $C_6$-$C_{30}$ linear, branched or cyclic alkyl alcohols and $C_6$-$C_{30}$ linear, branched or cyclic alkenyl alcohols comprising at least one carbon-carbon double bond, or a linear or branched low molecular weight polymer molecule selected from hydrogenated or non-hydrogenated poly(butadiene) or hydrogenated or non-hydrogenated poly(isoprene), and wherein the molecular weight of the organic alcohol is between 300-10000, preferably between 1000-5000 and most preferably between 1500 and 3000 grams/mole.

8. The integrated circuit of claim 1, further comprising a relative humidity sensor for cross-referencing the output of the $CO_2$ sensor.

9. The integrated circuit according to claim 1, further comprising at least one patterned metallization layer for interconnecting the plurality of circuit elements and a passivation layer over the at least one patterned metallization layer, wherein each electrode of the pair of electrodes is at least partially located on the passivation layer and conductively coupled to respective portions of the at least one patterned metallization layer.

10. The integrated circuit of claim 1, wherein gel-forming polymer in a range of 40-70% by weight relative to the total weight of the $CO_2$-permeable polymer matrix.

11. A composition for forming the $CO_2$-permeable polymer matrix of the integrated circuit of any of claim 1, the composition comprising:

a volatile solvent; and a gel-forming polymer, an organic alcohol, and an organic amidine or guanidine base dissolved in the volatile solvent.

12. The composition of claim 11, wherein the gel forming polymer is a block copolymer comprising at least one rigid block and at least one elastomeric block, wherein the at least one rigid block is optionally selected from polystyrene (PS) and poly(methylmethacrylate) (PMMA), and/or wherein at least one elastomeric block is individually selected from hydrogenated or non-hydrogenated poly (butadiene) (PEB; PB) or hydrogenated or non-hydrogenated poly(isoprene) (PEP; PI).

13. The composition of claim 11, wherein the volatile solvent is toluene, xylene or tetrahydrofuran.

14. An integrated circuit comprising:

a semiconductor substrate carrying a plurality of circuit elements; and a $CO_2$-sensor over the semiconductor substrate, the sensor comprising:

a pair of electrodes laterally separated from each other; and a $CO_2$-permeable polymer matrix at least partially covering the pair of electrodes, the $CO_2$-permeable polymer matrix immobilizing and encapsulating a $CO_2$-binding organic liquid comprising:

an organic alcohol; and an amidine or guanidine base, wherein the $CO_2$-permeable polymer matrix comprises a gel forming polymer, and wherein the $CO_2$-binding organic liquid provides for $CO_2$ sensitivity of the $CO_2$-sensor.

* * * * *